US012315638B2

United States Patent
Nakamura

(10) Patent No.: US 12,315,638 B2
(45) Date of Patent: May 27, 2025

(54) SURGERY SUPPORT SYSTEM, SURGERY SUPPORT METHOD, INFORMATION PROCESSING APPARATUS, AND INFORMATION PROCESSING PROGRAM

(71) Applicant: Sony Group Corporation, Tokyo (JP)

(72) Inventor: Naoto Nakamura, Tokyo (JP)

(73) Assignee: Sony Group Corporation, Tokyo (JP)

( * ) Notice: Subject to any disclaimer, the term of this patent is extended or adjusted under 35 U.S.C. 154(b) by 604 days.

(21) Appl. No.: 17/630,518

(22) PCT Filed: Mar. 27, 2020

(86) PCT No.: PCT/JP2020/014168
§ 371 (c)(1),
(2) Date: Jan. 27, 2022

(87) PCT Pub. No.: WO2021/029106
PCT Pub. Date: Feb. 18, 2021

(65) Prior Publication Data
US 2022/0246307 A1 Aug. 4, 2022

(30) Foreign Application Priority Data
Aug. 13, 2019 (JP) .................. 2019-148454

(51) Int. Cl.
*G06T 7/00* (2017.01)
*G16H 30/20* (2018.01)
*G16H 50/30* (2018.01)
(52) U.S. Cl.
CPC ........... *G16H 50/30* (2018.01); *G06T 7/0012* (2013.01); *G16H 30/20* (2018.01); *G06T 2207/10016* (2013.01); *G06T 2207/20081* (2013.01)

(58) Field of Classification Search
CPC ......... G06T 7/0012; G06T 2207/10016; G06T 2207/20081; G16H 50/30; G16H 30/20; G16H 30/40; G16H 40/63
See application file for complete search history.

(56) References Cited

U.S. PATENT DOCUMENTS

| 2019/0029757 A1 | 1/2019 | Roh et al. |
| 2019/0069957 A1 | 3/2019 | Barral |
| 2021/0015560 A1* | 1/2021 | Boddington ........... G16H 20/40 |

FOREIGN PATENT DOCUMENTS

| CN | 102117378 B | 7/2012 |
| CN | 102982238 B | 4/2016 |

(Continued)

OTHER PUBLICATIONS

Arvind et al. "Predicting Surgical Complications in Adult Patients Undergoing Anterior Cervical Discectomy and Fusion Using Machine Learning.", Neurospine, vol. 15(4), doi.org/10.14245/ns.1836248.124, Dec. 17, 2018, pp. 329-337 (Year: 2018).*

(Continued)

*Primary Examiner* — Jon Chang
(74) *Attorney, Agent, or Firm* — XSENSUS LLP

(57) ABSTRACT

A surgery support system according to the present disclosure includes an analysis unit that generates risk analysis information from a first surgery image acquired by an acquiring unit, by adopting the first surgery image to a trained model generated using learning data including a second surgery image that is a surgery image different from the first surgery image, the second surgery image having associated information on a complication risk due to surgery, and an output unit that outputs surgery support information that is based on the risk analysis information generated by the analysis unit, in a superimposed manner on the first surgery image.

20 Claims, 12 Drawing Sheets

(56) References Cited

FOREIGN PATENT DOCUMENTS

| | | | |
|---|---|---|---|
| CN | 106687959 A | 5/2017 | |
| CN | 107368670 A | 11/2017 | |
| CN | 108133755 A | 6/2018 | |
| CN | 108697304 A | 10/2018 | |
| CN | 109844868 A | 6/2019 | |
| JP | 2006320427 A | 11/2006 | |
| JP | 2010506629 A | 3/2010 | |
| JP | 2014042818 A | 3/2014 | |
| JP | 2016-42982 A | 4/2016 | |
| JP | 2018528040 A | 9/2018 | |
| WO | WO-2018089812 A | 5/2018 | |
| WO | 2018/155898 A1 | 8/2018 | |
| WO | WO-2018235533 A1 | 12/2018 | |
| WO | WO-2019116593 A1 | 6/2019 | |

OTHER PUBLICATIONS

International Search Report and Written Opinion mailed on Jul. 23, 2020, received for PCT Application PCT/JP2020/014168, Filed on Mar. 27, 2020, 9 pages.

* cited by examiner

FIG.7

| MODEL ID | INTENDED USE | MODEL DATA | ... |
|---|---|---|---|
| M1 | COMPLICATION RISK | MDT1 | ... |
| ... | ... | ... | ... |

START

S101
ACQUIRE FIRST SURGERY IMAGE

S102
GENERATE RISK ANALYSIS INFORMATION ON SURGERY IMAGE BY APPLYING FIRST SURGERY IMAGE TO TRAINED MODEL THAT IS GENERATED USING LEARNING DATA INCLUDING SECOND SURGERY IMAGE AND INCLUDING INFORMATION ON COMPLICATION RISK DUE TO SURGERY

S103
OUTPUT SURGERY SUPPORT INFORMATION BASED ON ANALYSIS INFORMATION IN SUPERIMPOSED MANNER ON SURGERY IMAGE

END

SURGERY SUPPORT SYSTEM, SURGERY SUPPORT METHOD, INFORMATION PROCESSING APPARATUS, AND INFORMATION PROCESSING PROGRAM

CROSS-REFERENCE TO RELATED APPLICATIONS

The present application is based on PCT/JP2020/014168 filed on Mar. 27, 2020, and claims priority to Japanese Application No. 2019-148454 filed on Aug. 13, 2019, the entire contents of each are incorporated herein by reference.

TECHNICAL FIELD

The present disclosure relates to a surgery support system, a surgery support method, an information processing apparatus, and an information processing program.

BACKGROUND ART

In a surgery room, various imaging means, such as an endoscope camera, a surgical field camera, and a surgical place camera, are used, and images (surgery images) captured by the imaging means are displayed during surgery. Further, the surgery images obtained by imaging performed by the imaging means are recorded for use for verification, confirmation, or the like after surgery.

CITATION LIST

Patent Literature

PTL 1: Japanese Laid-open Patent Publication No. 2016-42982

SUMMARY OF INVENTION

Technical Problem

In a conventional technology, a process that facilitates editing of videos of surgery is automatically performed. Specifically, chapter information indicating a timing at which input of an operation instruction on an imaging unit is received is automatically added, as metadata, to a surgery image.

However, in the conventional technology as described above, the metadata is added to the surgery image only at the time of editing the videos of surgery, in other words, only to facilitate the editing of the videos after the surgery, and therefore, further utilization of surgery images is desired. Further, complications related to surgery, such as surgical complications including ruptured suture, may occur due to surgery.

In view of the foregoing situations, in the present disclosure, a surgery support system, a surgery support method, an information processing apparatus, and an information processing program capable of appropriately outputting information for supporting surgery are provided.

Solution to Problem

Example embodiments of the present disclosure can provide information for supporting surgery, such as information used to predict a complication risk, in addition to providing the surgery image. The present disclosure is defined by the appended claims. According to an aspect of the present disclosure, an surgery support system is provided that includes (e.g. comprises): an acquiring unit configured to acquire a first surgery image that is a surgery image; an analysis unit configured to generate risk analysis information on the first surgery image by applying the first surgery image acquired by the acquiring unit to a trained model that is generated using learning data, the learning data including a second surgery image that is a surgery image different from the first surgery image and including information on a complication risk due to surgery; and an output unit configured to output surgery support information that is based on the risk analysis information generated by the analysis unit, in a superimposed manner on a surgery image such as the first surgery image. Other example embodiments provide a surgery support system including (e.g. comprising): an acquiring unit configured to acquire a first surgery image; an analysis unit configured to generate risk analysis information from the first surgery image by applying the first surgery image acquired by the acquiring unit to a trained model associating image features of the first surgery image with information on a complication risk due to surgery; and an output unit configured to output surgery support information that is based on the risk analysis information generated by the analysis unit, for example in a superimposed manner on the first surgery image.

BRIEF DESCRIPTION OF DRAWINGS

FIG. 7 is a diagram illustrating an example of a model information storage unit according to the embodiment of the present disclosure.

FIG. 8 is a flowchart illustrating the flow of a surgery support process according to the embodiment of the present disclosure.

DESCRIPTION OF EMBODIMENTS

Figure 1:
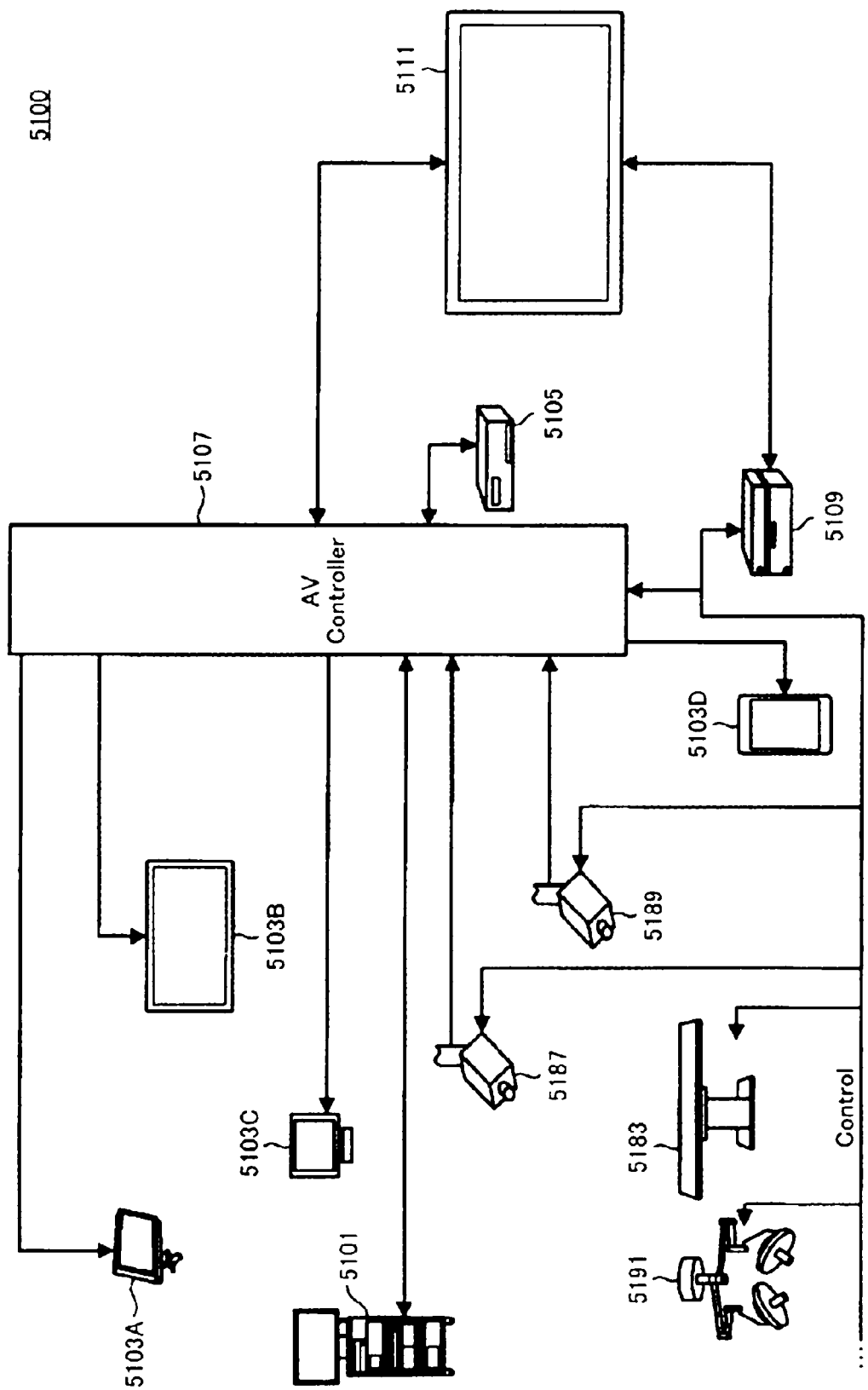
FIG. 1 is a diagram schematically illustrating an overall configuration of a surgery room system.

Exemplary embodiments of the present disclosure will be described in detail below based on the drawings. A surgery support system, a surgery support method, an information processing apparatus, and an information processing program according to the present disclosure are not limited by the embodiments below. Further, in each of the embodiments described below, the same components will be denoted by the same reference symbols, and repeated explanation of the components will be omitted. In so far as embodiments of the disclosure are described as being implemented, at least in part, by software-controlled data processing apparatus, it will be appreciated that a non-transitory machine-readable medium carrying such software, such as an optical disk, a magnetic disk, semiconductor memory or the like, is also considered to represent an embodiment of the present disclosure.

Note that description will be given in the following order.
1. System configuration example
1-1. Configuration of surgery support system according to embodiment
2. Overview
2-1. Complication
2-2. Surgery images including first and second surgery images
2-3. Complication risk information
3. Details of embodiment
3-1. Configuration of information processing apparatus according to embodiment
3-2. Example of output apparatus according to embodiment
3-3. Procedure of surgery support process according to embodiment
3-4. Overview of surgery support process according to embodiment
3-5. Output example of surgery support information
3-5-1. Display of surgery support information
3-5-2. Two-step output
3-6. Example of process performed by surgery support system
4. Other embodiments
4-1. Other configuration examples
4-1-1. Modification of surgery support system
4-1-2. Modification of information processing apparatus
4-2. Output mode of surgery support information
4-3. Others
5. Effects according to present disclosure
6. Hardware configuration

1. System Configuration Example

First, a configuration example as one example of a surgery support system according to an embodiment of the present disclosure will be described with reference to the drawings. Examples of the surgery support system according to the embodiment of the present disclosure include various systems. A surgery support system 1 includes a surgery room system 5100 and an information processing apparatus 100, details of which will be described later with reference to FIG. 5. The information processing apparatus 100 generates risk analysis information on a surgery image by using a trained model (hereinafter, may be simply referred to as a "model") that predicts a complication risk. The surgery room system 5100 includes a display apparatus 5155 as an output apparatus that functions as an output unit for outputting surgery support information that is based on the risk analysis information generated by the information processing apparatus 100. In the following, the display apparatus 5155 will be described as one example of the output apparatus, but the output apparatus is not limited to the display apparatus 5155, and may be any apparatus, such as display apparatuses 5103A to 5103D or a centralized operation panel 5111, as long as the apparatus functions as the output unit that outputs the surgery support information. Further, the output unit that outputs the surgery support information may be installed separately from the surgery room system 5100, which will be described in detail later.

Furthermore, the surgery support system 1 may include the plurality of surgery room systems 5100. In this case, the information processing apparatus 100 communicates with each of the surgery room systems 5100 and performs a surgery support process to be described later. Moreover, if the surgery support system 1 deals with the single surgery room system 5100, the information processing apparatus 100 may be included in the surgery room system 5100. In this case, the surgery support system 1 may be the surgery room system 5100. In the following, first, a configuration example of the surgery room system will be mainly described as one example of a constituent element of the surgery support system according to the embodiment of the present disclosure.

FIG. 1 is a diagram schematically illustrating an overall configuration of the surgery room system 5100 to which a technology according to the present disclosure is applicable. With reference to FIG. 1, the surgery room system 5100 is constructed by connecting apparatuses installed in a surgery room to one another in a cooperative manner via an audio-visual controller (AV Controller) 5107 and a surgery room control apparatus 5109.

Various apparatuses may be installed in the surgery room. In FIG. 1, as one example, a group of various apparatuses 5101 used for endoscopic surgery, a ceiling camera 5187 that is arranged on the ceiling of the surgery room and captures an image of an object in the hand of a surgeon, a surgical place camera 5189 that is arranged on the ceiling of the surgery room and captures an image of the entire surgery room, the plurality of display apparatuses 5103A to 5103D, a recorder 5105, a patient bed 5183, and an illumination lamp 5191 are illustrated.

Among the apparatuses as described above, the group of apparatuses 5101 belongs to an endoscopic surgery system 5113, and includes an endoscope, a display apparatus that displays an image captured by the endoscope, and the like. Each of the apparatuses that belong to the endoscopic surgery system 5113 may also be referred to as a medical apparatus. In contrast, the display apparatuses 5103A to 5103D, the recorder 5105, the patient bed 5183, and the illumination lamp 5191 are installed in, for example, the surgery room separately from the endoscopic surgery system 5113. Each of the apparatuses that do not belong to the endoscopic surgery system 5113 may also be referred to as a non-medical apparatus. The audiovisual controller 5107 and/or the surgery room control apparatus 5109 control operation of the medical apparatuses and the non-medical apparatuses in cooperation with each other.

In some examples, the audiovisual controller 5107 integrally controls processes related to image display in the medical apparatuses and the non-medical apparatuses. Specifically, among the apparatuses included in the surgery room system 5100, the group of apparatuses 5101, the ceiling camera 5187, and the surgical place camera 5189 may be apparatuses (hereinafter, may be referred to as transmission source apparatuses) that have functions to transmit information (hereinafter, may be referred to as display information) to be displayed during surgery. Further, the display apparatuses 5103A to 5103D may be apparatuses to which the display information is output (hereinafter, may be referred to as output destination apparatuses). Furthermore, the recorder 5105 may be an apparatus that correspond to both of the transmission source apparatus and the output destination apparatus. The audiovisual controller 5107 has a function to control operation of the transmission source apparatuses and the output destination apparatuses, acquire the display information from the transmission source apparatuses, transmit the display information to the output destination apparatuses, and display or store the display information. The display information includes various images that are captured during surgery, various kinds of information on surgery (for example, body information on a patient, past examination results, information on surgical procedures, and the like), and the like.

Specifically, the group of apparatuses 5101 may transmit, as the display information, information on an image of a surgical site located inside a body cavity of a patient captured by an endoscope to the audiovisual controller 5107. Further, the ceiling camera 5187 may transmit, as the display information, information on an image of an object in the hand of a surgeon captured by the ceiling camera 5187. Furthermore, the surgical place camera 5189 may transmit, as the display information, information on an image of a situation in the entire surgery room captured by the surgical place camera 5189. If the surgery room system 5100 includes other apparatuses having imaging functions, the audiovisual controller 5107 may acquire, as the display information, information on images captured by the other apparatuses from the other apparatus.

Alternatively, for example, the audiovisual controller 5107 may record information on images that are captured in the past in the recorder 5105. The audiovisual controller 5107 is able to acquire, as the display information, the information on the images that are captured in the past from the recorder 5105. Meanwhile, various kinds of information on surgery may also be recorded in advance in the recorder 5105.

In some examples, the audiovisual controller 5107 causes at least one of the display apparatuses 5103A to 5103D serving as the output destination apparatuses to display the acquired display information (in other words, an image captured during surgery or various kinds of information on surgery). In the example illustrated in the drawing, the display apparatus 5103A is a display apparatus that is hang on the ceiling of the surgery room, the display apparatus 5103B is a display apparatus that is mounted on the wall surface of the surgery room, the display apparatus 5103C is a display apparatus that is placed on a table in the surgery room, and the display apparatus 5103D is a mobile apparatus (for example, a tablet personal computer (PC)) that has a display function.

While not illustrated in FIG. 1, the surgery room system 5100 may include an external apparatus located outside the surgery room. Examples of the external apparatus located outside the surgery room include a server connected to networks constructed inside and outside a hospital, a PC used by a medical staff, and a projector installed in a conference room in the hospital. If the external apparatus is located outside the hospital, the audiovisual controller 5107 may be able to cause a display apparatus located in a different hospital to display the display information via a video conference system or the like, for conducting telemedicine.

In some examples, the surgery room control apparatus 5109 integrally controls processes other than processes related to image display in the non-medical apparatuses. For example, the surgery room control apparatus 5109 controls drive of the patient bed 5183, the ceiling camera 5187, the surgical place camera 5189, and the illumination lamp 5191.

In some examples, the surgery room system 5100 includes the centralized operation panel 5111, and a user is able to give an instruction on image display to the audiovisual controller 5107 and gives an instruction on operation of the non-medical apparatuses to the surgery room control apparatus 5109, via the centralized operation panel 5111. The centralized operation panel 5111 is constructed by arranging a touch panel on a display screen of the display apparatus.

Figure 2:
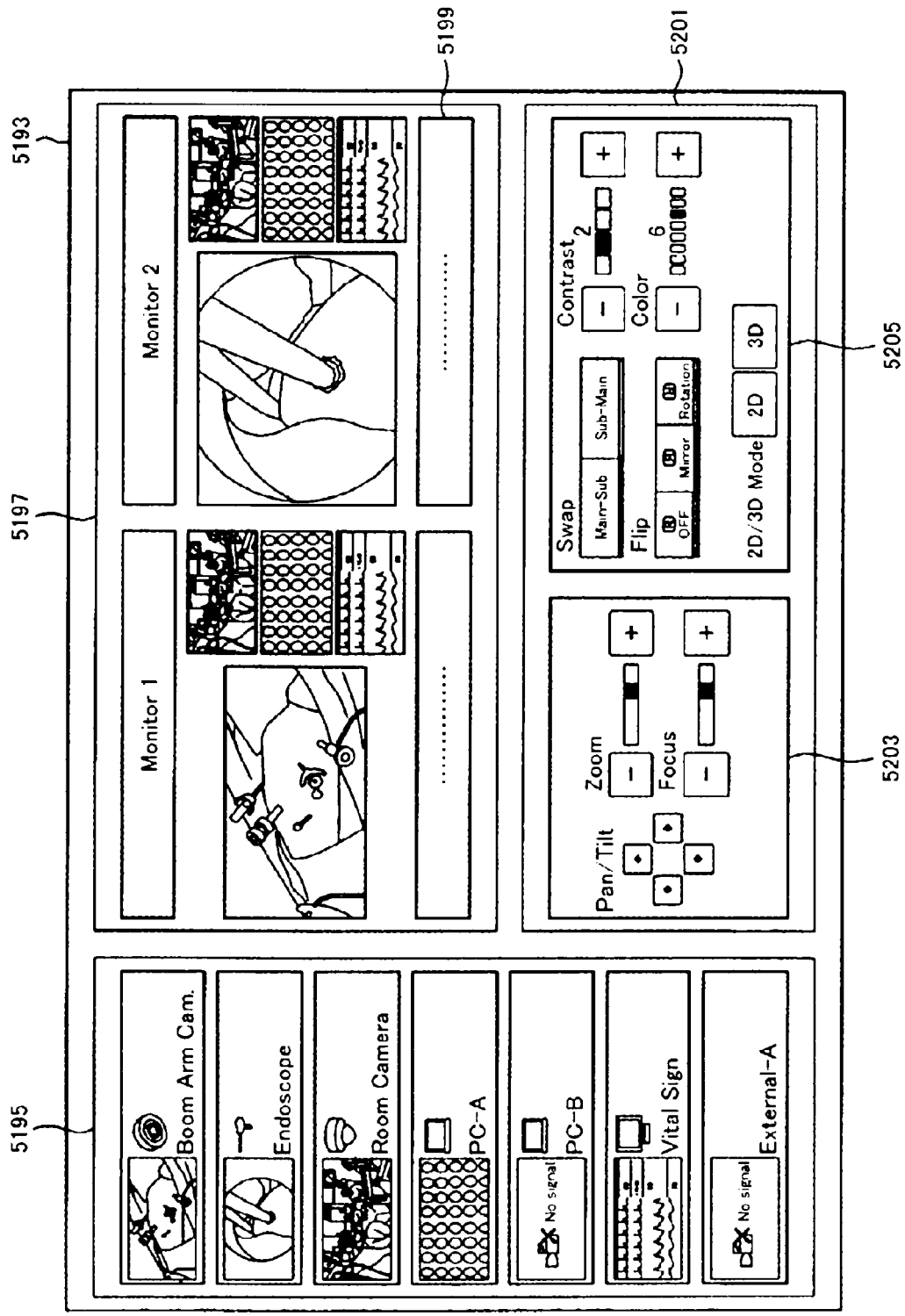
FIG. 2 is a diagram illustrating a display example of an operation screen in a centralized operation panel.

FIG. 2 is a diagram illustrating a display example of an operation screen in the centralized operation panel 5111. In FIG. 2, as one example, an operation screen corresponding to a case in which two display apparatuses are arranged as the output destination apparatuses in the surgery room system 5100 is illustrated. With reference to FIG. 2, an operation screen 5193 includes a transmission source selection region 5195, a preview region 5197, and a control region 5201.

In the transmission source selection region 5195, the transmission source apparatuses included in the surgery room system 5100 and thumbnail screens representing display information held in the transmission source apparatuses are displayed in an associated manner. The user is able to select display information to be displayed on the display apparatus from any of the transmission source apparatuses displayed in the transmission source selection region 5195.

In the preview region 5197, previews of screens displayed on the two display apparatuses (Monitor 1 and Monitor 2) serving as the output destination apparatuses are displayed. In the example illustrated in the drawing, four images are displayed in a picture-in-picture (PinP) manner in the single display apparatus. The four images correspond to the display information transmitted from the transmission source apparatus that is selected in the transmission source selection region 5195. One of the four images is displayed as a main image with a relatively large size, and the remaining three images are displayed as sub images with relatively small sizes. The user is able to switch between the main image and the sub images by appropriately selecting regions in which the four images are displayed. Further, a status display region 5199 is arranged below the region in which the four images are displayed, and a status of surgery (for example, surgery duration, body information on a patient, or the like) is appropriately displayed in this region.

The control region 5201 includes a transmission source operation region 5203 in which graphical user interface (GUI) components for performing operation on the transmission source apparatus are displayed, and an output destination operation region 5205 in which GUI components for performing operation on the output destination apparatus are displayed. In the example illustrated in the drawing, GUI components for performing various kinds of operation (pan, tilt, and zoom) on a camera in the transmission source apparatus having an imaging function are arranged in the transmission source operation region 5203. The user is able to control operation of the camera in the transmission source apparatus by appropriately selecting the GUI components. While not illustrated in the drawings, if the transmission source apparatus selected in the transmission source selection region 5195 is a recorder (in other words, if images that are recorded in the past in the recorder are displayed in the preview region 5197), GUI components for performing operation, such as replay, stop, fastrewind, and fast-forward, on the images may be arranged in the transmission source operation region 5203.

Further, GUI components for performing various kinds of operation (swap, flip, color adjustment, contrast adjustment, and switching between 2D-display and 3D-display) on the display apparatus serving as the output destination apparatus are arranged in the output destination operation region 5205. The user is able to control display on the display apparatus by appropriately selecting the GUI components.

The operation screen displayed on the centralized operation panel 5111 is not limited to the example as illustrated in the drawing, and the user may be allowed to perform, via the centralized operation panel 5111, input operation on each of apparatuses that are included in the surgery room system 5100 and that are controlled by the audiovisual controller 5107 and the surgery room control apparatus 5109.

Figure 3:
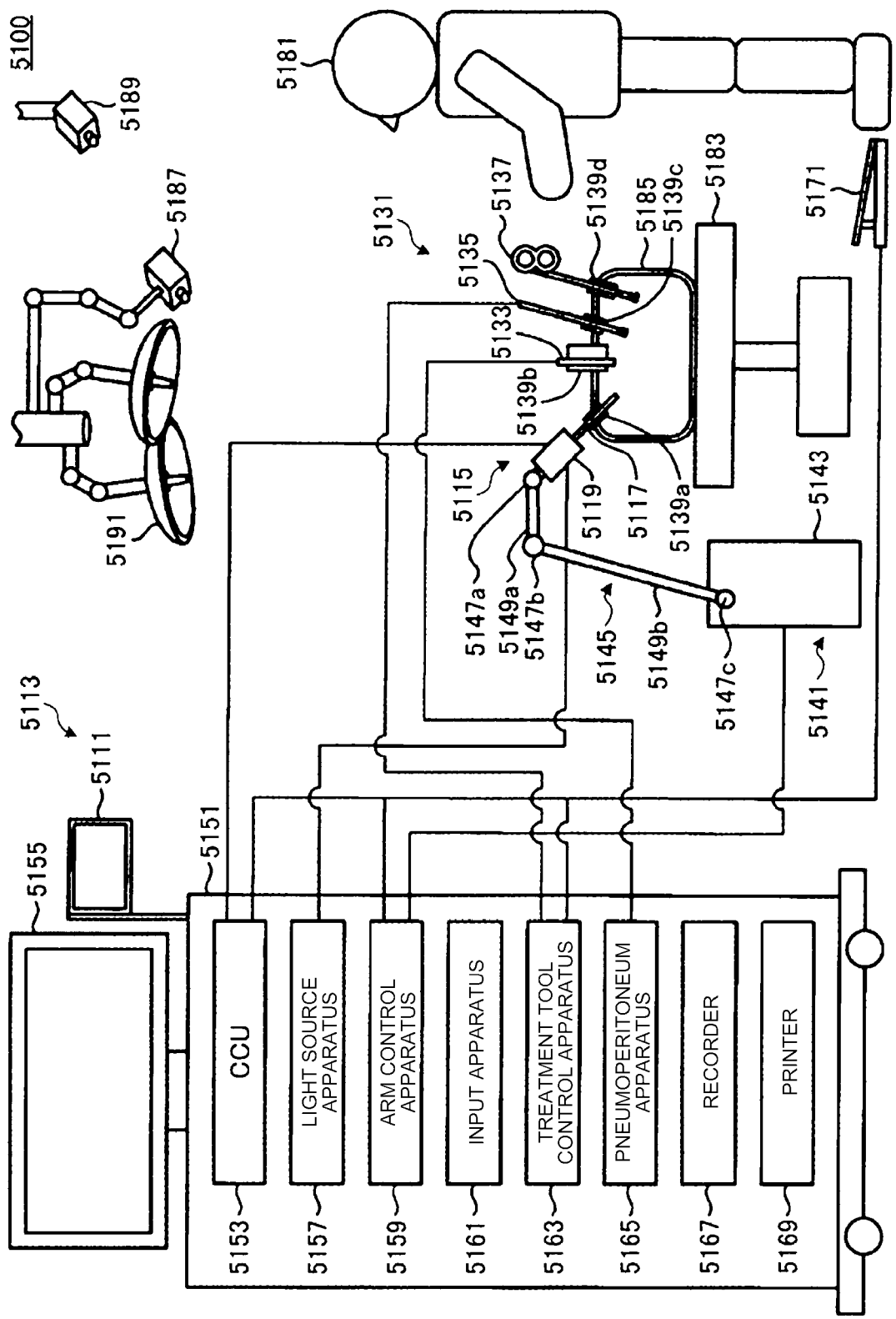
FIG. 3 is a diagram illustrating an example of a situation of surgery for which the surgery room system is adopted.

FIG. 3 is a diagram illustrating an example of a situation of surgery for which the surgery room system as described above is adopted. The ceiling camera 5187 and the surgical place camera 5189 are arranged on the ceiling of the surgery room and able to capture an image of an object in the hand of a surgeon (doctor) who performs treatment on an affected area of a patient 5185 on the patient bed 5183 and an image of a situation in the entire surgery room. The ceiling camera 5187 and the surgical place camera 5189 may have a magnification adjustment function, a focal length adjustment function, an imaging direction adjustment function, and the like. The illumination lamp 5191 is arranged on the ceiling of the surgery room and illuminates at least an object in the hand of a surgeon 5181. The illumination lamp 5191 may be able to appropriately adjust an intensity of illumination light, a wavelength (color) of the illumination light, a light illumination direction, and the like.

The endoscopic surgery system 5113, the patient bed 5183, the ceiling camera 5187, the surgical place camera 5189, and the illumination lamp 5191 are connected to one another in a cooperative manner via the audiovisual controller 5107 and the surgery room control apparatus 5109 (not illustrated in FIG. 3) as illustrated in FIG. 1. The centralized operation panel 5111 is arranged in the surgery room, and, as described above, the user is able to appropriately operate the apparatuses located in the surgery room via the centralized operation panel 5111.

A configuration of the endoscopic surgery system 5113 will be described in detail below. As illustrated in the drawing, the endoscopic surgery system 5113 includes an endoscope 5115, other surgery tools 5131, a support arm apparatus 5141 that supports the endoscope 5115, and a cart 5151 on which various apparatuses for endoscopic surgery are mounted.

In the endoscopic surgery, cylindrical hole-opening tools called trocars 5139*a* to 5139*d* are introduced to make a plurality of punctures into the abdominal wall, instead of opening the abdominal cavity by cutting the abdominal wall. Then, a lens barrel 5117 of the endoscope 5115 and the other surgery tools 5131 are inserted into the body cavity of the patient 5185 through the trocars 5139*a* to 5139*d*. In the example illustrated in the drawing, an insufflation tube 5133, an energy treatment tool 5135, and a forceps 5137 are inserted, as the other surgery tools 5131, into the body cavity of the patient 5185. Further, the energy treatment tool 5135 is a treatment tool for cutting and loosening tissue, sealing a blood vessel, and the like with high-frequency current or ultrasonic vibration. However, the surgery tools 5131 illustrated in the drawing are mere examples, and as the surgery tools 5131, for example, various surgery tools, such as tweezers and retractors, which are generally used in the endoscopic surgery, may be used.

An image of a surgical site inside the body cavity of the patient 5185 captured by the endoscope 5115 is displayed on the display apparatus 5155. The surgeon 5181 views the image of the surgical site displayed on the display apparatus 5155 in real time and performs treatment, such as removal of an affected area, using the energy treatment tool 5135 or the forceps 5137. While not illustrated in the drawing, the insufflation tube 5133, the energy treatment tool 5135, and the forceps 5137 are supported by the surgeon 5181, an assistant, or the like during the surgery.

(Support Arm Apparatus)

The support arm apparatus 5141 includes an arm section 5145 that extends from a base section 5143. In the example illustrated in the drawing, the arm section 5145 includes joint sections 5147*a*, 5147*b*, and 5147*c*, and links 5149*a* and 5149*b*, and is driven by being controlled by an arm control apparatus 5159. The arm section 5145 supports the endoscope 5115 and controls a position and posture of the endoscope 5115. With this configuration, it is possible to stably fix the position of the endoscope 5115.

(Endoscope)

The endoscope 5115 includes the lens barrel 5117, a certain region of which with a predetermined length from a distal end is to be inserted into the body cavity of the patient 5185, and a camera head 5119, which is connected to a proximal end of the lens barrel 5117. In the example illustrated in the drawing, the endoscope 5115 that is configured as what is called a rigid scope having the rigid lens barrel 5117 is illustrated; however, the endoscope 5115 may be configured as what is called a flexible scope having the flexible lens barrel 5117.

An opening in which an objective lens is fitted is arranged on the distal end of the lens barrel 5117. A light source apparatus 5157 is connected to the endoscope 5115, and light generated by the light source apparatus 5157 is guided to the distal end of the lens barrel by a light guide that is extended inside the lens barrel 5117, and applied to an observation target inside the body cavity of the patient 5185 via the objective lens. The endoscope 5115 may be a forward-viewing endoscope, a forward-oblique viewing endoscope, or a side-viewing endoscope.

An optical system and an imaging element are arranged inside the camera head 5119, and the optical system condenses reflected light (observation light) from the observation target toward the imaging element. The imaging element performs photoelectric conversion on the observation light, and an electrical signal corresponding to the observation light, that is, an image signal corresponding to an observation image, is generated. The image signal is transmitted, as RAW data, to a camera control unit (CCU) 5153. The camera head 5119 has a function to adjust a magnification and a focal length by appropriately driving the optical system.

To cope with a stereoscopic view (3D-display) or the like for example, it may be possible to arrange a plurality of imaging elements on the camera head 5119. In this case, a plurality of relay optical systems are arranged inside the lens barrel 5117 in order to guide the observation light to the respective imaging elements.

(Various Apparatuses Mounted on Cart)

The CCU 5153 is constructed by a central processing unit (CPU), a graphics processing unit (GPU), or the like, and integrally controls operation of the endoscope 5115 and the display apparatus 5155. Specifically, the CCU 5153 performs various kinds of image processing, such as a developing process (demosaicing process), on an image signal received from the camera head 5119, in order to display an image based on the image signal. The CCU 5153 provides the image signal subjected to the image processing to the display apparatus 5155. Further, the audiovisual controller 5107 illustrated in FIG. 1 is connected to the CCU 5153. The CCU 5153 provides the image signal subjected to the image processing to the audiovisual controller 5107. Furthermore, the CCU 5153 transmits a control signal to the camera head 5119 and controls drive of the camera head 5119. The control signal may include information on imaging conditions, such as a magnification and a focal length. The information on the imaging conditions may be input via an input apparatus 5161 or may be input via the centralized operation panel 5111 as described above.

The display apparatus 5155 displays the image based on the image signal subjected to the image processing by the CCU 5153, under the control of the CCU 5153. If the endoscope 5115 is compatible with high-resolution imaging, such as 4K (3840 horizontal pixels×2160 vertical pixels) or 8K (7680 horizontal pixels×4320 vertical pixels), and/or if the endoscope 5115 is compatible with 3D-display, an apparatus that can perform high-resolution display and/or 3D-display is used as the display apparatus 5155 in accordance with the respective compatibilities. If the apparatus is compatible with high-resolution imaging, such as 4K or 8K, it is possible to achieve increased immersion by adopting an apparatus with a size of 55 inch or larger as the display apparatus 5155. Further, it may be possible to arrange the plurality of display apparatuses 5155 with different resolution and sizes for different uses.

The light source apparatus 5157 is constructed by a light source, such as a light emitting diode (LED), and supplies illumination light for capturing an image of a surgical site to the endoscope 5115.

The arm control apparatus 5159 is constructed by a processor, such as a CPU, operates in accordance with a predetermined program, and controls drive of the arm section 5145 of the support arm apparatus 5141 in accordance with a predetermined control method.

The input apparatus 5161 is an input interface for the endoscopic surgery system 5113. The user is able to input various kinds of information and instructions to the endoscopic surgery system 5113 via the input apparatus 5161. For example, the user inputs, via the input apparatus 5161, various kinds of information on surgery, such as body information on a patient or information on procedures of surgery. Further, for example, the user inputs, via the input apparatus 5161, an instruction to drive the arm section 5145, an instruction to change imaging conditions (a type of illumination light, a magnification, a focal length, and the like) of the endoscope 5115, an instruction to drive the energy treatment tool 5135, and the like.

Types of the input apparatus 5161 are not specifically limited, and various known input apparatuses may be adopted as the input apparatus 5161. As the input apparatus 5161, for example, a mouse, a keyboard, a touch panel, a switch, a foot switch 5171 and/or a lever may be adopted. If the touch panel is used as the input apparatus 5161, the touch panel may be arranged on a display surface of the display apparatus 5155.

Alternatively, the input apparatus 5161 may be, for example, a device that can be worn by the user, such as a glasses wearable device or a head mounted display (HMD), and various kinds of input are performed in accordance with gestures and lines of sight of the user detected by the device. Further, the input apparatus 5161 includes a camera that can detect motion of the user, and performs various kinds of input in accordance with gestures and lines of sight of the user detected from videos captured by the camera. Furthermore, the input apparatus 5161 includes a microphone that can collect voice of the user, and performs various kinds of input based on voice via the microphone. In this manner, the input apparatus 5161 is configured to be able to input various kinds of information in a non-contact manner, so that it is possible to allow, in particular, a user (for example, the surgeon 5181) who is in a clean zone to operate apparatuses located in a dirty zone in a non-contact manner. Further, the user is able to operate the apparatuses without releasing his/her hand from a carrying surgery tool, so that it is possible to improve the convenience of the user.

A treatment tool control apparatus 5163 controls drive of the energy treatment tool 5135 for tissue ablation, incision, sealing of a blood vessel, or the like. A pneumoperitoneum apparatus 5165 feeds gas into the body cavity via the insufflation tube 5133 to inflate the body cavity of the patient 5185, to thereby ensure a visual field of the endoscope 5115 and ensure an operating space for the surgeon. A recorder 5167 is an apparatus that can record various kinds of information on surgery. A printer 5169 is an apparatus that can print various kinds of information on surgery in various formats, such as a text, an image, or a graph.

A particularly characteristic configuration of the endoscopic surgery system 5113 will be described in detail below.

(Support Arm Apparatus)

The support arm apparatus 5141 includes the base section 5143 as a base board, and the arm section 5145 extending from the base section 5143. In the example illustrated in the drawing, the arm section 5145 includes the plurality of joint sections 5147a, 5147b, and 5147c and the plurality of links 5149a and 5149b that are connected by the joint section 5147b; however, in FIG. 3, the configuration of the arm section 5145 is simplified for the sake of simplicity. In reality, shapes, numbers, and arrangement of the joint sections 5147a to 5147c and the links 5149a and 5149b, directions of rotation shafts of the joint sections 5147a to 5147c, and the like may be appropriately set to ensure desired flexibility of the arm section 5145. For example, the arm section 5145 may be preferably configured to have flexibility of 6 level or higher. With this configuration, it becomes possible to freely move the endoscope 5115 in a movable range of the arm section 5145, so that it is possible to insert the lens barrel 5117 of the endoscope 5115 from a desired direction into the body cavity of the patient 5185.

Actuators are arranged in the joint sections 5147a to 5147c, and the joint sections 5147a to 5147c are configured to be able to rotate around predetermined rotation shafts in accordance with the drive of the actuators. The drive of the actuators is controlled by the arm control apparatus 5159, so that a rotation angle of each of the joint sections 5147a to 5147c is controlled and the drive of the arm section 5145 is controlled. Accordingly, it becomes possible to control the position and the posture of the endoscope 5115. In this case, the arm control apparatus 5159 is able to control the drive of the arm section 5145 using various well-known control method, such as force control or position control.

For example, when the surgeon 5181 appropriately inputs operation via the input apparatus 5161 (including the foot switch 5171), the arm control apparatus 5159 may appropriately control the drive of the arm section 5145 in accordance with the input operation, and the position and the posture of the endoscope 5115 may be controlled. With this control, it is possible to first move the endoscope 5115 arranged on the distal end of the arm section 5145 from an arbitrary position to another arbitrary position, and thereafter fixedly support the endoscope 5115 at the moved position. The arm section 5145 may be operated by what is called a master-slave system. In this case, the arm section 5145 may be remotely operated by a user via the input apparatus 5161 that is installed at a place away from the surgery room.

Further, if the force control is adopted, the arm control apparatus 5159 may perform what is called power assist control to receive an external force from the user and drive the actuator of each of the joint sections 5147a to 5147c such that the arm section 5145 smoothly moves in accordance with the external force. With this configuration, when the user moves the arm section 5145 while directly touching the arm section 5145, it is possible to move the arm section 5145 with a relatively small force. Therefore, it becomes possible to more intuitively move the endoscope 5115 with easier operation, so that it is possible to improve the convenience of the user.

Here, in general, in endoscopic surgery, the endoscope 5115 is supported by a doctor called a scopist. In contrast, with use of the support arm apparatus 5141, it becomes possible to more reliably fix the position of the endoscope 5115 without manual intervention, so that it becomes possible to stably obtain an image of a surgical site and perform surgery smoothly.

Meanwhile, the arm control apparatus 5159 need not always be mounted on the cart 5151. Further, the arm control apparatus 5159 need not always be a single apparatus. For example, the arm control apparatus 5159 may be mounted on each of the joint sections 5147a to 5147c of the arm section 5145 of the support arm apparatus 5141, and the plurality of arm control apparatuses 5159 may operate in cooperation with one another and control drive of the arm section 5145.

(Light Source Apparatus)

The light source apparatus 5157 supplies illumination light to the endoscope 5115 when capturing an image of a surgical site. The light source apparatus 5157 includes, for example, an LED, a laser light source, or a white light source that is constructed by a combination of an LED and a laser light source. In this case, if the white light source is constructed by a combination of RGB laser light sources, it is possible to control output intensity and an output timing of each of colors (each wavelength) with high accuracy, and therefore, in the light source apparatus 5157, it is possible to adjust a white balance of a captured image. Further, in this case, by illuminating an observation target with laser light from each of the RGB laser light sources in a time-sharing manner and controlling the drive of the imaging element of the camera head 5119 in synchronization with illumination timings, it is possible to capture respective images corresponding to RGB in a time-sharing manner. With this method, it is possible to obtain a color image without arranging a color filter on the imaging element.

Furthermore, it may be possible to control the drive of the light source apparatus 5157 such that the intensity of output light is changed at predetermined time intervals. By controlling the drive of the imaging element of the camera head 5119 in synchronization with a timing to change the intensity of light, obtaining images in a time-sharing manner, and combining the obtained images, it is possible to generate a high dynamic range image in which what is called blocked up shadows and blown out highlights do not occur.

Moreover, the light source apparatus 5157 may be configured to be able to supply light in a predetermined wavelength band or in another form corresponding to so-called special light observation. In an example of special light observation, for example, what is called narrow band imaging is performed, in which light in a narrower band than that of illumination light (in other words, white light) used in normal observation is applied by using wavelength dependency of light absorption in body tissues and an image of a predetermined tissue, such as a blood vessel in a superficial portion of a mucous membrane, is captured with high contrast. Alternatively, in another example of special light observation, it may be possible to perform fluorescence observation to obtain an image by fluorescence that is generated by applying excitation light. In the fluorescence observation, it may be possible to illuminate a body tissue with excitation light and observe fluorescence received from the body tissue (autofluorescence observation), or it may be possible to locally inject reagent, such as indocyanine green (ICG), into a body tissue, illuminate the body tissue with excitation light corresponding to a fluorescence wavelength of the reagent, and acquire a fluorescent image, for example. The light source apparatus 5157 may be configured to be able to supply the narrow band light and/or the excitation or other light corresponding to the special light observation as described above.

In other examples of so-called special light observation, the light source apparatus 5157 need not always be configured as described above, but may be configured in various other ways. The light source apparatus 5157 may be a laser light source that is used for speckle observation (detection of a blood flow based on speckle). In this manner, it may be possible to observe deep parts of a living body through the speckle observation using the light source apparatus 5157 that is the laser light source. In this case, the observation of the deep parts of the living body is performed by using a technique related to speckle imaging using speckle interference or the like. Accordingly, the surgery room system 5100 may generate an image (speckle image) through the speckle observation. If the speckle observation as described above is performed, the light source apparatus 5157 may be configured to be able to supply light (laser light or the like) corresponding to the speckle observation. Meanwhile, in other examples of this technique, the surgery room system 5100 may include a different light source apparatus used for the speckle observation, in addition to the light source apparatus 5157 used for the special light observation.

For example, Japanese Laid-open Patent Publication No. 2016-151524 discloses speckle observation using a laser light source. For example, the surgery room system 5100 may generate a leveled speckle image from a speckle enhanced image corresponding to each illumination condition, through the method as disclosed in Japanese Laid-open Patent Publication No. 2016-151524.

(Camera Head and CCU)

Figure 4:
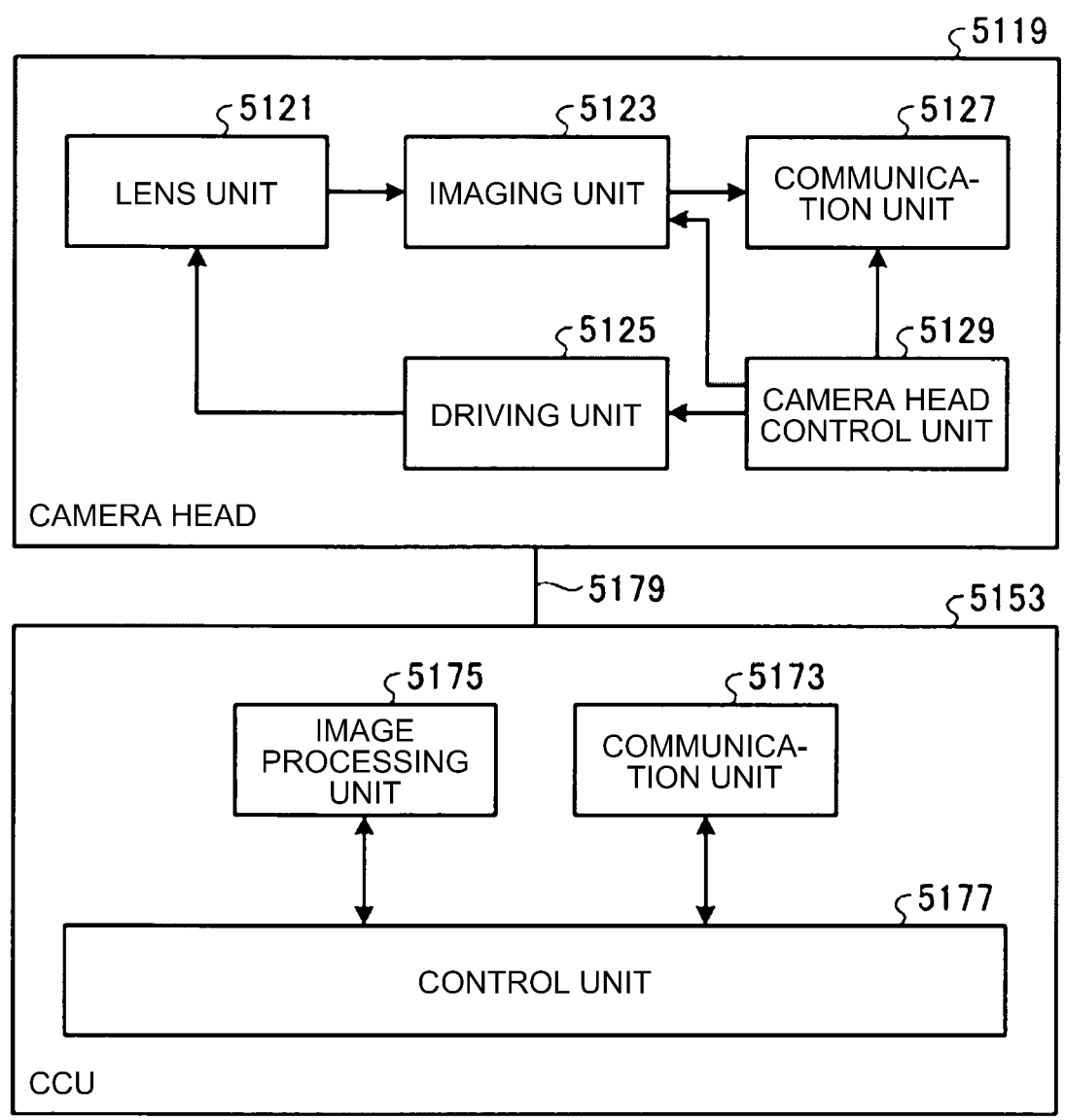
FIG. 4 is a block diagram illustrating an example of a functional configuration of a camera head and a CCU illustrated in FIG. 3.

Functions of the camera head 5119 and the CCU 5153 of the endoscope 5115 will be described in detail below with reference to FIG. 4. FIG. 4 is a block diagram illustrating an example of functional configurations of the camera head 5119 and the CCU 5153 illustrated in FIG. 3.

With reference to FIG. 4, the camera head 5119 includes, as the functions thereof, a lens unit 5121, an imaging unit 5123, a driving unit 5125, a communication unit 5127, and a camera head control unit 5129. Further, the CCU 5153 includes, as the functions thereof, a communication unit 5173, an image processing unit 5175, and a control unit 5177. The camera head 5119 and the CCU 5153 are connected to each other such that they can bi-directionally communicate with each other via a transmission cable 5179.

First, the functional configuration of the camera head 5119 will be described. The lens unit 5121 is an optical system arranged in a connection part connected to the lens barrel 5117. Observation light that has entered from the distal end of the lens barrel 5117 is guided to the camera head 5119 and enters the lens unit 5121. The lens unit 5121 is constructed by a combination of a plurality of lenses including a zoom lens and a focus lens. Optical characteristics of the lens unit 5121 are adjusted such that observation light is condensed on a light-receiving surface of an imaging element of the imaging unit 5123. Further, the zoom lens and the focus lens are configured such that positions thereof on an optical axis can be moved to adjust a magnification and a focal point of a captured image.

The imaging unit 5123 is configured with the imaging element and is arranged on a subsequent stage of the lens unit 5121. The observation light that has passed through the lens unit 5121 is condensed on the light-receiving surface of the imaging element, and an image signal corresponding to an observation image is generated through photoelectric conversion. The image signal generated by the imaging unit 5123 is provided to the communication unit 5127.

As the imaging element constituting the imaging unit 5123, for example, a complementary metal oxide semiconductor (CMOS) type image sensor that has Bayer arrangement and that can capture color images may be used. Meanwhile, as the imaging element, for example, a device that is compatible with capturing of an image with high resolution of 4K or higher may be used. By obtaining an image of a surgical site at high resolution, the surgeon 5181 is able to more precisely recognize a condition of the surgical site, so that it is possible to perform the surgery more smoothly.

Further, the imaging element constituting the imaging unit 5123 is configured to include a pair of imaging elements to obtain image signals for right and left eyes to cope with 3D-display. By performing 3D-display, the surgeon 5181 is able to accurately recognize a depth of a body tissue in the surgical site. If the imaging unit 5123 is configured as a multi-sensor system, the plurality of lens units 5121 are arranged in accordance with the respective imaging elements.

Furthermore, the imaging unit 5123 need not always be mounted on the camera head 5119. For example, the imaging unit 5123 may be arranged immediately after the objective lens inside the lens barrel 5117.

The driving unit 5125 is configured with an actuator, and moves the zoom lens and the focus lens of the lens unit 5121 by a predetermined distance along the optical axis under the control of the camera head control unit 5129. Accordingly, it is possible to appropriately adjust a magnification and a focal point of a captured image captured by the imaging unit 5123.

The communication unit 5127 is configured with a communication apparatus for transmitting and receiving various kinds of information to and from the CCU 5153. The communication unit 5127 transmits an image signal obtained from the imaging unit 5123 as RAW data to the CCU 5153 via the transmission cable 5179. In this case, to display the captured image of the surgical site with low latency, it is preferable to transmit the image signal through optical communication. When surgery is performed, the surgeon 5181 performs the surgery while observing a condition of an affected area using the captured image, and therefore, it is demanded to display a video of a surgical site in real time as best as possible to perform the surgery more safely and more reliably. When the optical communication is performed, a photoelectric conversion module that converts an electrical signal to an optical signal is arranged in the communication unit 5127. An image signal is converted to an optical signal by the photoelectric conversion module, and thereafter transmitted to the CCU 5153 via the transmission cable 5179.

Further, the communication unit 5127 receives, from the CCU 5153, a control signal for controlling drive of the camera head 5119. The control signal includes information on an imaging condition, such as information for designating a frame rate of a captured image, information for designating an exposure value at the time of imaging, and/or information for designating a magnification and a focal point of the captured image. The communication unit 5127 provides the received control signal to the camera head control unit 5129. Meanwhile, the control signal from the CCU 5153 may be transmitted through optical communication. In this case, a photoelectric conversion module that converts an optical signal to an electrical signal is arranged in the communication unit 5127, and, the control signal is converted to an electrical signal by the photoelectric conversion module and thereafter provided to the camera head control unit 5129.

The imaging conditions as described above, such as the frame rate, the exposure value, the magnification, and the focal point, are automatically set by the control unit 5177 of the CCU 5153 on the basis of the acquired image signal. In other words, what is called an automatic exposure (AE) function, an automatic focus (AF) function, and an automatic white balance (AWB) function are mounted on the endoscope 5115.

The camera head control unit 5129 controls the drive of the camera head 5119 on the basis of the control signal that is received from the CCU 5153 via the communication unit 5127. For example, the camera head control unit 5129 controls the drive of imaging element of the imaging unit 5123 on the basis of the information for designating the frame rate of the captured image and/or the information for designating exposure at the time of imaging. Further, for example, the camera head control unit 5129 appropriately moves the zoom lens and the focus lens of the lens unit 5121 via the driving unit 5125 on the basis of the information for designating the magnification and the focal point of the captured image. The camera head control unit 5129 may further include a function to store information for identifying the lens barrel 5117 and the camera head 5119.

By arranging the components, such as the lens unit 5121 and the imaging unit 5123, inside a sealed structure with high air tightness and high waterproof property, it is possible to ensure the resistance of the camera head 5119 to an autoclave sterilization process.

The functional configuration of the CCU 5153 will be described below. The communication unit 5173 is configured with a communication apparatus for transmitting and receiving various kinds of information to and from the camera head 5119. The communication unit 5173 receives an image signal that is transmitted from the camera head 5119 via the transmission cable 5179. In this case, as described above, the image signal may be preferably transmitted through optical communication. In this case, to cope with the optical communication, a photoelectric conversion module that converts an optical signal to an electrical signal is arranged in the communication unit 5173. The communication unit 5173 provides the image signal converted to the electrical signal to the image processing unit 5175.

Further, the communication unit 5173 transmits a control signal for controlling the drive of the camera head 5119 to the camera head 5119. The control signal may be transmitted through optical communication.

The image processing unit 5175 performs various kinds of image processing on the image signal that is RAW data transmitted from the camera head 5119. Examples of the image processing include various kinds of well-known signal processing, such as a developing process, a high-quality image processing (band enhancement processing, super-resolution processing, noise reduction (NR) processing and/or shake correction processing), and/or enlargement processing (electronic zoom processing). Further, the image processing unit 5175 performs wave detection processing on the image signal to implement AE, AF, and AWB.

The image processing unit 5175 is configured with a processor, such as a CPU or a GPU, and the processor operates in accordance with a predetermined program, so that the image processing and the wave detection processing as described above can be performed. If the image processing unit 5175 is configured with a plurality of GPUs, the image processing unit 5175 appropriately divides information on the image signal, and performs image processing in parallel using the plurality of GPUs.

The control unit 5177 performs various kinds of control related to imaging of a surgical site by the endoscope 5115 and display of the captured image. For example, the control unit 5177 generates a control signal for controlling the drive of the camera head 5119. In this case, if the user has input an imaging condition, the control unit 5177 generates the control signal based on the input performed by the user. Alternatively, if the endoscope 5115 has the AE function, the AF function, and the AWB function, the control unit 5177 appropriately calculates an optimal exposure value, an optimal focal length, and an optimal white balance in accordance with a result of the wave detection processing performed by the image processing unit 5175, and generates a control signal.

Further, the control unit 5177 causes the display apparatus 5155 to display an image of the surgical site on the basis of the image signal subjected to the image processing by the image processing unit 5175. In this case, the control unit 5177 recognizes various objects in the image of the surgical site by using various image recognition techniques. For example, by detecting a shape, a color, or the like of an edge of an object included in the image of the surgical site, the control unit 5177 is able to recognize a surgery tool, such as a forceps, a specific site of a living body, bleeding, mist in the case of use of the energy treatment tool 5135, and the like. The control unit 5177, when causing the display apparatus 5155 to display the image of the surgical site, displays various kinds of surgery support information in a superimposed manner on the first surgery image of the surgical site, by using a recognition result. The surgery support information is displayed in a superimposed manner and provided to the surgeon 5181, so that it is possible to perform the surgery more safely and more reliably.

The transmission cable 5179 that connects the camera head 5119 and the CCU 5153 is an electrical signal cable corresponding to electrical signal communication, an optical fiber corresponding to optical communication, or a composite cable of the above-described cables.

In the example illustrated in the drawing, communication is performed in a wired manner using the transmission cable 5179, but communication between the camera head 5119 and the CCU 5153 may be performed in a wireless manner. If the communication between the camera head 5119 and the CCU 5153 is performed in a wireless manner, it is not necessary to arrange the transmission cable 5179 in the surgery room, so that it is possible to resolve a situation in which movement of a medical staff in the surgery room is disturbed by the transmission cable 5179.

One example of the surgery room system 5100 to which the technology according to the present disclosure is applicable has been described above. In the description above, as one example, the case has been described in which the surgery room system 5100 is adopted to the endoscopic surgery system 5113 as a medical system, but the configuration of the surgery room system 5100 is not limited to the above-described example. For example, the surgery room system 5100 may be adopted to an examination flexible endoscope system or a microscopic surgery system, instead of the endoscopic surgery system 5113.

<1-1. Configuration of Surgery Support System According to Embodiment>

Figure 5:
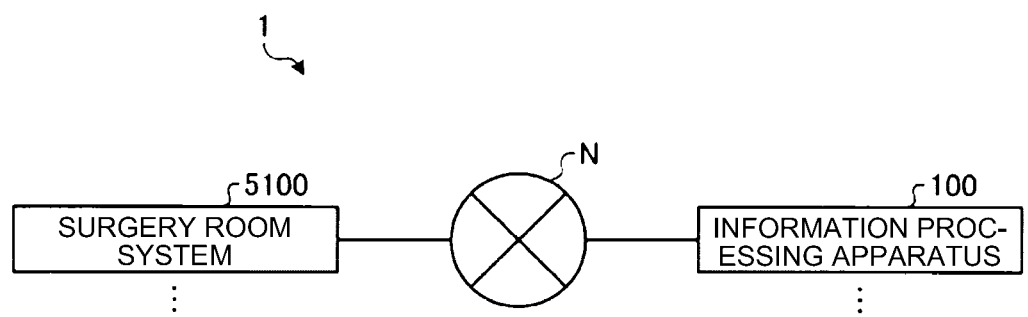
FIG. 5 is a diagram illustrating a configuration example of the surgery support system according to an embodiment of the present disclosure.

The surgery support system 1 illustrated in FIG. 5 will be described. As illustrated in FIG. 5, the surgery support system 1 includes the surgery room system 5100 and the information processing apparatus 100. The surgery room system 5100 and the information processing apparatus 100 are communicably connected in a wired or wireless manner via a predetermined communication network (network N). FIG. 5 is a diagram illustrating a configuration example of the surgery support system according to the embodiment. The surgery support system 1 illustrated in FIG. 5 may include the plurality of surgery room systems 5100 or the plurality of information processing apparatuses 100. For example, the surgery support system 1 implements various kinds of information processing related to support for surgery. A target person for whom surgery is supported is not limited to a surgeon, but may be various medical professionals involved in the surgery. The medical professionals described herein include staffs, such as scopists, anesthesiologists, assistants, and nurses, who are involved in various surgeries.

The surgery room system 5100 is a system including various apparatuses used to perform surgery as illustrated in FIG. 1 to FIG. 4. For example, the surgery room system 5100 includes the display apparatus 5155 as an output apparatus that outputs surgery support information that is based on the risk analysis information such that the surgery support information is superimposed on the first surgery image. The display apparatus 5155 displays the surgery support information that is based on the risk analysis information such that the surgery support information is superimposed on the first surgery image.

The information processing apparatus 100 is used to provide services related to support for surgery. The information processing apparatus 100 performs various kinds of information processing related to the surgery support system. The information processing apparatus 100 is a computer that acquires a first surgery image as a surgery image, applies the acquired first surgery image to a trained model, and generates risk analysis information on the first surgery image.

Meanwhile, the information processing apparatus 100 may be a server apparatus or the like that is arranged in a facility (for example, a hospital or the like) in which the surgery room system 5100 is installed, or a server apparatus (for example, a cloud server or the like) that is arranged outside the facility, as long as the apparatus can execute predetermined information processing. In this manner, in the surgery support system 1, the surgery support system 1 may be operated using an on-premise system or a cloud system. In other words, the information processing apparatus 100 in the surgery support system 1 may be installed at any position as long as conditions or the like for operation of the surgery support system are met.

2. Overview

An overview of the technology according to the present disclosure will be described below. At least some example embodiments of the present disclosure can provide a surgery support system that, for example, determines a surgical complication risk, such as ruptured suture, using an artificial intelligence (AI) and displays a determination result in real time during surgery. Here, a surgery complication risk due to ruptured suture is caused by defective anastomosis, hypertension at an anastomotic site, or impaired blood flow, and normally occurs due to defective surgical operation (a suture position or a suture method).

For example, the surgical complication risk due to ruptured suture is disclosed in the following Literature: "Special topic subject I: Preventive measure against ruptured suture II: Preventive measure against ruptured suture after surgery of colorectal cancer" (Journal of the Japan Society of Coloproctology 62: 812-817, 2009).

In example embodiments of the surgery support system 1, by causing the AI to learn recorded past surgery videos and positions and grades of postsurgical complications, it is possible to predict a complication risk, such as ruptured suture, from an intraoperative image.

The surgery support system 1 adopts a determination model for determining a complication risk, such as ruptured suture, to a surgery video captured by the endoscope, determines the complication risk, such as riskiness of suture in the surgery video, and provide a determination result as surgery support information (also referred to as "support information") to a surgeon. By providing, as the support information, a risk probability, risk exposure, and information on a site of occurrence of a complication, such as a site of ruptured suture, it becomes possible to potentially reduce the chances of a complication risk due to ruptured suture or the like from occurring in the surgery taking place with support from the support information.

For example, the surgery support system 1 may be adopted as an intraoperative ruptured suture automatic analysis system in a digestive tract endoscopic surgery using an analysis technique based on deep learning. In this case, the surgery support system 1 may be adopted as a next-generation in-hospital video system that, in real time, transmits videos from intraoperative endoscopic videos to a server via a network and superimposes a determination result of automatic analysis based on a deep learning technique onto a high-quality low-latency video.

<2-1. Complication>

Incidents that occur during surgery are largely classified into medical accidents due to negligence (mistakes), such as leaving gauze, and complications that occur at about a constant rate in association with surgery. Occurrence of complications leads to second surgery, additional treatment, longer hospitalization, and the like, so that influence and burden of hospitals, patients, and medical costs increase. Therefore, prediction of a complication risk makes it possible to potentially reduce the occurrence of second or subsequent surgery, additional treatment, longer hospitalization, and the like and reduce the influence and burden of hospitals, patients, and medical costs. Therefore, the surgery support system 1 adopts complications among incidents that occur during surgery as targets for risk prediction. Further, the surgery support system 1 mainly adopts surgical complications, such as ruptured suture, intestinal obstruction, wound infection, and intraperitoneal abscess, as targets for risk prediction.

In this manner, the surgery support system 1 performs a process by adopting, as targets, complications that occur with a fixed probability when surgery is performed, instead of negligence (mistakes) made by a surgeon or the like. The surgery support system 1 may adopt various complications as targets as long as the complications are applicable, in addition to the above-described complications. For example, the surgery support system 1 may adopt general complications, such as pneumonia and pulmonary embolism, bleeding, and lymphorrhea as targets for risk prediction. The surgery support system 1 as described above is effective for various complications, and, in particular, effective for complications that are detected after surgery and are less likely to be detected at the time of surgical closure.

<2-2. Surgery Images Including First and Second Surgery Images>

The surgery image is an image related to surgery, such as an image captured by the endoscope. This term may refer to live (or near-live, for example low latency as discussed here) image information which may be presented to a surgeon or other operator as "first surgery images" showing the ongoing conduct of a surgical operation. The term "second surgery image" may refer to image information having associated metadata or other information indicating whether or not (or the extent to which) a complication or other outcome occurred, and which can be used to train a model to identify potential complications or other outcomes in the first surgery images or other captured images of the prevailing progress of the operation. For example, a second surgery image may be image information including a site that becomes a cause of a surgical complication. The second surgery image may be image information in which a site that becomes a cause of a surgical complication is captured. The second surgery image may be image information in which an image of a suture site is captured. The second surgery image may be image information in which an image of a bleeding site is captured. The surgery image may be an image in which various targets are captured, as long as the image is related to surgery. The surgery image may be a moving image (video), a special light observation image, or the like. The first surgery image described herein corresponds to an image that is output such that the surgery support information is superimposed thereon. For example, the first surgery image corresponds to a surgery image that is captured in surgery that is continued at the time the surgery support information is output. Further, the second surgery image described herein corresponds to an image that is used to generate a trained model. For example, the second surgery image corresponds to a surgery image that was captured in past surgery that was performed at an earlier time than the time at which the surgery support information is output.

As described above, the first surgery image and the second surgery image are relative concepts; therefore, in some cases, a single surgery image may first serve as the first surgery image and thereafter serve as the second surgery image (for example to train and/or update a model for use with future instances of the first surgery images). For example, if a certain surgery image is adopted as an output target on which the surgery support information is superimposed, the certain surgery image serves as the first surgery image. Further, if a certain surgery image is included in learning data that is used to generate a trained model, the certain surgery image serves as the second surgery image. In the following, when the first surgery image and the second surgery image need not be specifically distinguished from each other, they may be simply described as "surgery images".

It is preferable that the surgery image is a high-resolution image with 4K or higher because determination accuracy can be improved. By using high resolution, such as 4K or 8K, for the surgery image, it is possible to improve the determination accuracy. The surgery image may be an image that is captured using so-called special light and/or using electromagnetic waves with wavelengths other than visible light. Further, if a technology, such as narrow band imaging (NBI), is used, the surgery image may be an image (special light observation image) that is observed using special light, such as narrow band light. In other examples the surgery image may be an image (speckle image) that is captured using a technique related to speckle imaging as described above. Further, the surgery image may be a suture image in which a suture portion appears.

<2-3. Complication Risk Information>

Information (also referred to as "complication risk information") that is related to a complication risk and used as the learning data may be various kinds of information as long as the information indicates a complication risk. The complication risk information may be information indicating a complication probability or information indicating severity of a complication risk. If the complication risk information includes the information indicating the complication probability, the complication risk information may include binary information indicating whether a complication is present or absent. For example, the information indicating the complication probability may be information that is set to "1" if a complication is present and set to "0" if a complication is absent.

For example, the information processing apparatus 100 adopts a surgery image of certain surgery as input data (for example as so-called ground truth input data), learns the complication risk information indicating presence or absence of a complication in the certain surgery as correct answer information, and generates a model that outputs a larger score for a higher complication probability in accordance with input of a surgery image. For example, the information processing apparatus 100 adopts a surgery image of certain surgery as input data, learns the complication risk information indicating presence or absence of a complication in the certain surgery as the correct answer information, and generates a model that outputs a value closer to "1" for higher complication probability in accordance with input of a surgery image.

Meanwhile, the information indicating the complication probability is not limited to the binary information, but may be any kind of information as long as the information indicates the complication probability. For example, the information indicating the complication probability may be a continuous value in a range of 0 to 1 (0 to 100%). For example, the information indicating the complication probability may be any value (for example, 70% or the like) indicating an event probability from among values of 0 to 100%.

If the complication risk information is the information indicating the severity of a complication risk, the complication risk information may include information that indicates the severity of a complication risk based on five-grade scale. For example, the information indicating the severity of a complication risk may be information on a five-grade scale based on the JCOG criteria, for example by a mapping defined for example by a predetermined or a learned mapping table from the event probability discussed above.

For example, the JCOG criteria are disclosed as follows.

"JCOG postoperative complications criteria (Clavien-Dindo Classification)" <http://www.jcog.jp/doctor/tool/JCOG_Clavien-Dindo_ver2.0.pdf>

For example, the information processing apparatus 100 adopts a surgery image of certain surgery as input data, learns the complication risk information indicating severity of a complication in the certain surgery as correct answer information, and generates a model that outputs a larger score for higher severity of the complication in accordance with input of a surgery image. For example, the information processing apparatus 100 adopts a surgery image of certain surgery as input data, learns the complication risk information indicating severity of a complication in the certain surgery as the correct answer information, and generates a model that outputs a value closer to "5" for higher severity of the complication in accordance with input of a surgery image.

Further, the complication risk information may include information indicating a site related to occurrence of a risk. The complication risk information may include information on a risk occurrence site. The complication risk information may include information on a suture site. The complication risk information may include information on a bleeding site. The complication risk information may include information indicating a site at which a complication risk is highly likely to occur in a corresponding surgery image. The complication risk information may include information indicating a site at which a risk has occurred in a corresponding surgery image. The complication risk information may be annotation (metadata) added to image data (surgery image).

For example, the information processing apparatus 100 adopts a surgery image as input data, learns the complication risk information indicating a site at which a complication has occurred in the surgery image as the correct answer information, and generates a model that outputs information indicating a site at which a complication is highly likely to occur in the surgery image in accordance with input of a surgery image. For example, by performing learning using a group (first image group) of surgery images in which complications have occurred and a group (second image group) of surgery images in which complications have not occurred, the information processing apparatus 100 is able to generate a model that outputs information indicating a site at which a complication is highly likely to occur with respect to a surgery image that includes the site. For example, the information processing apparatus 100 generates a model by learning, as the correct answer information, images in the first image group and the complication risk information indicating a site of occurrence. For example, the information processing apparatus 100 generates a model by learning, as the correct answer information, images in the second image group and the complication risk information indicating that there is no site of occurrence.

3. Details of Embodiment

<3-1. Configuration of Information Processing Apparatus According to Embodiment>

Figure 6:
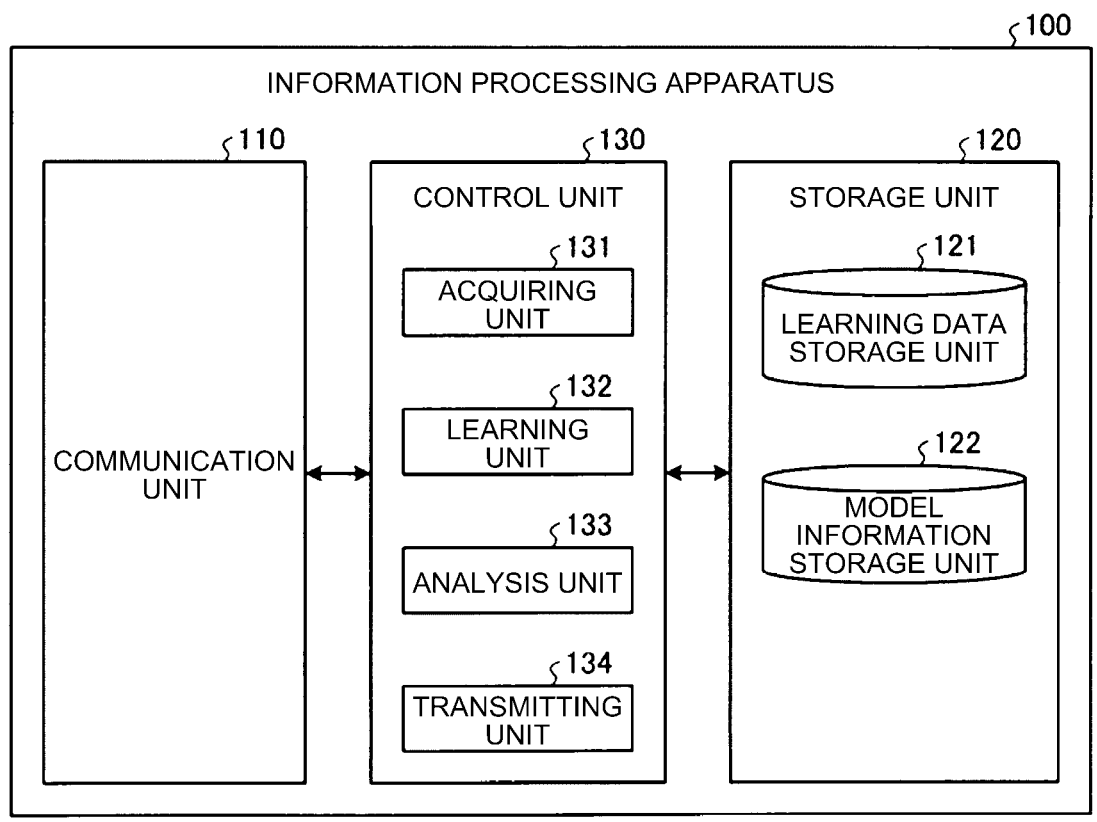
FIG. 6 is a diagram illustrating a configuration example of an information processing apparatus according to the embodiment of the present disclosure.

A configuration of the information processing apparatus 100 as one example of the information processing apparatus that executes the information processing according to the embodiment will be described below. FIG. 6 is a diagram illustrating a configuration example of the information processing apparatus 100 according to the embodiment of the present disclosure.

As illustrated in FIG. 6, the information processing apparatus 100 includes a communication unit 110, a storage unit 120, and a control unit 130. The information processing apparatus 100 may include an input unit (for example, a keyboard, a mouse, or the like) that receives various kinds of operation from an administrator or the like of the information processing apparatus 100, and a display unit (for example, a liquid crystal display or the like) for displaying various kinds of information.

The communication unit 110 is realized by, for example, a network interface card (NIC) or the like. The communication unit 110 is connected to the network N (see FIG. 5) in a wired or wireless manner, and transmits and receives information to and from the surgery room system 5100. For example, the communication unit 110 may transmit and receive information to and from each of the apparatuses, such as the display apparatus 5155 and the CCU 5153, of the surgery room system 5100.

The storage unit 120 is realized by, for example, a semiconductor memory device, such as a random access memory (RAM) or a flash memory, or a storage device, such as a hard disk or an optical disk. The storage unit 120 according to the embodiment includes, as illustrated in FIG. 6, a learning data storage unit 121 and a model information storage unit 122.

The learning data storage unit 121 stores therein various kinds of information (learning data) on data that is used for learning. The learning data storage unit 121 stores therein teaching data that is used to generate a model. The learning data storage unit 121 stores therein learning data information including data that is used as an input, and including information, such as the correct answer information (correct answer label) and an output (prediction label), that corresponds to the data.

The learning data storage unit 121 stores therein learning data, in which data of a surgery image (second surgery image) that is used as an input and information (correct answer label) that is related to a complication risk due to surgery (second surgery) corresponding to the surgery image are associated with each other. The learning data storage unit 121 stores therein, as learning data (teaching data), a combination of the second surgery image that is a past surgery image and the information on a complication risk due to surgery corresponding to the second surgery image.

The learning data storage unit 121 is not limited to the above-described example, and may store therein various kinds of information depending on purposes. The learning data storage unit 121 may store therein meta-information (also referred to as "surgery attribute information") corresponding to a surgery image, in association with the surgery image. In this case, the information processing apparatus 100 may generate a model that adopts the surgery image and the surgery attribute information as inputs.

For example, the learning data storage unit 121 may store therein the surgery attribute information including information on a patient (also referred to as "patient information") to be subjected to surgery corresponding to the surgery image, in association with the surgery image. The patient information may include attribute information on the patient. For example, the patient information may include various kinds of information, such as age, sex, race, and health. The patient information is acquired from, for example, a hospital information system (HIS), an electronic medical record (EMR, may also be referred to as an electronic health record), or the like.

For example, the learning data storage unit 121 may store therein the surgery attribute information including information (also referred to as "surgeon information") on a surgeon who performs surgery corresponding to the surgery image, in association with the surgery image. The surgeon information may include attribute information on the surgeon. For example, the surgeon information may include various kinds of attribute information, such as age, sex, and backgrounds, on the surgeon.

Further, the learning data storage unit 121 may store therein, as the learning data, feature information on a surgery video. The learning data storage unit 121 may store therein, as the learning data, information indicating at least one of a change of manipulation and a change of a surgery scene. The learning data storage unit 121 may store therein, as the learning data, information on a suture process including at least one of a suture method and a suture position. The learning data storage unit 121 may store therein, as the learning data, information on the suture process that is detected based on a trajectory of a surgical tool. The learning data storage unit 121 may store therein, as the learning data, information on a suture process that is detected based on a temporal change of a position of a distal end of a surgical tool. The learning data storage unit 121 may store therein, as the learning data, feature information that is detected based on operating time of surgery.

For example, the learning data storage unit 121 may be a database in which teaching data (learning data) with annotation of a risk of ruptured suture and a ruptured suture portion is stored. Further, the information processing apparatus 100 may acquire the learning data by accessing a database. In this case, the information processing apparatus 100 need not necessarily include the learning data storage unit 121. For example, the information processing apparatus 100 may access a trained database with annotation of a risk of ruptured suture and a ruptured suture portion, and acquire learning data with annotation of the risk of the ruptured suture and the ruptured suture portion. Therefore, in other words, references in the context of the surgery support system to a trained model and to source data such as second surgery images by which such a model is trained do not necessarily imply that the support system itself provides means or other arrangements operable to perform the training process; a pre-trained model may be used by the surgery support system.

The model information storage unit 122 according to the embodiment stores therein information on a model. For example, the model information storage unit 122 stores therein information (model data) on an already-trained model (model) that is learned (generated) by a learning process. FIG. 7 is a diagram illustrating an example of a model information storage unit according to the embodiment. FIG. 7 illustrates an example of the model information storage unit 122 according to the embodiment. In the example illustrated in FIG. 7, the model information storage unit 122 includes items of "model ID", "intended use", and "model data". In such examples, embodiments of the disclosure can provide a surgery support system including: an acquiring unit configured to acquire a first surgery image; an analysis unit configured to generate risk analysis information from the first surgery image by applying the first surgery image acquired by the acquiring unit to a trained model associating image features of the first surgery image with information on a complication risk due to surgery (for example, a pre-trained model as discussed above); and an output unit configured to output surgery support information that is based on the risk analysis information generated by the analysis unit, for example in a superimposed manner on the first surgery image.

The "model ID" indicates identification information for identifying a model. The "intended use" indicates an intended use of a corresponding model. The "model data" indicates data of a model. In the example illustrated in FIG. 7, conceptual information, such as "MDT1", is stored in the "model data", but in reality, various kinds of information, such as information on a network included in the model and functions, which constitute the model may be included.

In the example illustrated in FIG. 7, it is indicated that a model (model M1) identified by a model ID of "M1" is used for a "complication risk". Further, it is indicated that model data of the model M1 is model data MDT1.

Meanwhile, the model information storage unit 122 may store therein various kinds of information depending on purposes, in addition to the above-described information.

Referring back to FIG. 6, the explanation will be continued. The control unit 130 is realized by, for example, causing a central processing unit (CPU), a micro processing unit (MPU), or the like to execute a program (for example, the information processing program according to the present disclosure or the like) that is stored inside the information processing apparatus 100, by using a random access memory (RAM) or the like as a work area. Further, the control unit 130 is a controller, and is realized by, for example, an integrated circuit, such as an application specific integrated circuit (ASIC) or a field programmable gate array (FPGA).

As illustrated in FIG. 6, the control unit 130 includes an acquiring unit 131, a learning unit 132, an analysis unit 133, and a transmitting unit 134, and implements or executes functions and operation of a surgery support process as described below. The internal configuration of the control unit 130 is not limited to the configuration as illustrated in FIG. 6, and other configurations may be adopted as long as the information processing to be described later is performed. In addition, the connection relation of the processing units included in the control unit 130 is not limited to the connection relation as illustrated in FIG. 6, and any other connection relation may be adopted.

The acquiring unit 131 acquires various kinds of information. The acquiring unit 131 acquires various kinds of information from an external information processing apparatus. The acquiring unit 131 acquires various kinds of information from the surgery room system 5100. The acquiring unit 131 acquires various kinds of information from other information processing apparatuses, such as a voice recognition server.

In some examples, the acquiring unit 131 acquires various kinds of information from the storage unit 120. The acquiring unit 131 acquires various kinds of information from the learning data storage unit 121 and the model information storage unit 122.

For example, the acquiring unit 131 may acquire a model. In some examples, the acquiring unit 131 acquires the model from an external information processing apparatus that provides the model or the storage unit 120. For example, the acquiring unit 131 acquires the model M1 or the like from the model information storage unit 122.

In some examples, the acquiring unit 131 acquires various kinds of information learned by the learning unit 132. The acquiring unit 131 acquires various kinds of information analyzed by the analysis unit 133. In some examples, the acquiring unit 131 acquires various kinds of information calculated by the analysis unit 133. The acquiring unit 131 acquires various kinds of information generated by the analysis unit 133. In some examples, the acquiring unit 131 acquires various kinds of information determined by the analysis unit 133.

In some examples, the acquiring unit 131 acquires the first surgery image [that is a surgery image]. In some examples, the acquiring unit 131 acquires a trained model that is generated using learning data including information on a complication risk due to second surgery corresponding to the second surgery image.

In some examples, the acquiring unit 131 acquires the first surgery image that is high-quality low-latency image information that meets an image quality condition on image quality and a latency condition on latency. In some examples, the acquiring unit 131 acquires the first surgery image that is image information with resolution of 4K or higher. In some examples, the acquiring unit 131 acquires the first surgery image that is a special light observation image.

In some examples, the acquiring unit 131 acquires the second surgery image that is image information including a site that becomes a cause of a surgical complication. In some examples, the acquiring unit 131 acquires the second surgery image that is image information including at least one of a suture site and a bleeding site. In some examples, the acquiring unit 131 acquires the second surgery image that is image information including a site that is detected by image recognition.

In some examples, the acquiring unit 131 acquires the second surgery image that is a special light observation image. In some examples, the acquiring unit 131 acquires the second surgery image that is an image in which an internal state of a suture site or a bleeding site is visualized.

In some examples, the acquiring unit 131 acquires information related to a complication risk that is information indicating at least one of a probability and severity of a complication. In some examples, the acquiring unit 131 acquires the probability that is binary information indicating whether a complication is present or absent. In some examples, the acquiring unit 131 acquires the severity that is five-grade information indicating the degree of impact of a complication.

In some examples, the acquiring unit 131 acquires information on a complication risk that is information on a risk occurrence site. In some examples, the acquiring unit 131 acquires information on a risk occurrence site that is information on at least one of a suture site and a bleeding site.

In some examples, the acquiring unit 131 may acquire a trained model that is generated using the second surgery image that is image information including a site that becomes a cause of a surgical complication. In some examples, the acquiring unit 131 acquires a trained model that is generated using the second surgery image that is information including at least one of a suture site and a bleeding site.

In some examples, the acquiring unit 131 acquires a trained model that is generated using the second surgery image that is information including a site detected by image recognition. In some examples, the acquiring unit 131 acquires a trained model that is generated using the second surgery image that is a special light observation image. In some examples, the acquiring unit 131 acquires a trained model that is generated using the second surgery image that is an image in which an internal state of a suture site or a bleeding site is visualized.

In some examples, the acquiring unit 131 acquires a trained model that is generated using information related to a complication risk that is information indicating at least one of a probability and severity of a complication. In some examples, the acquiring unit 131 acquires a trained model that is generated using a probability that is binary information indicating whether a complication is present or absent. In some examples, the acquiring unit 131 acquires a trained model that is generated using severity that is five-grade information indicating a degree of impact of a complication.

In some examples, the acquiring unit 131 acquires a trained model that is generated using information on a complication risk that is information on a risk occurrence site. In some examples, the acquiring unit 131 acquires a trained model that is generated using information on a risk occurrence site that is information on at least one of a suture site and a bleeding site.

In some examples, the acquiring unit 131 acquires input data that is for the trained model and that is a surgery video. In some examples, the acquiring unit 131 acquires learning data that is a surgery video. In some examples, the acquiring unit 131 acquires input data that is for a trained model and that is a time-series image. In some examples, the acquiring unit 131 acquires learning data that is a time-series image.

In some examples, the acquiring unit 131 acquires meta-information (surgery attribute information) corresponding to a surgery image. In some examples, the acquiring unit 131 acquires the surgery attribute information from the storage unit 120 or an external information processing apparatus. For example, the acquiring unit 131 acquires the surgery attribute information including patient information on a patient (such as surgical outcome information) to be subjected to surgery corresponding to a surgery image. For example, the acquiring unit 131 acquires the surgery attribute information including surgeon information on a surgeon who performs surgery corresponding to a surgery image. For example, if the acquiring unit 131 acquires the surgery attribute information from an external information processing apparatus, the acquiring unit 131 stores the information in the storage unit 120. For example, if the acquiring unit 131 acquires the surgery attribute information corresponding to the second surgery image from an external information processing apparatus, the acquiring unit 131 stores the acquired surgery attribute information in the learning data storage unit 121 in association with the second surgery image.

In some examples, the learning unit 132 performs a learning process. In some examples, the learning unit 132 performs various kinds of learning. In some examples, the learning unit 132 learns (generates) a model. In some examples, the learning unit 132 learns various kinds of information on a model or the like. In some examples, the learning unit 132 generates a model by learning. In some examples, the learning unit 132 learns a model using techniques related to various kinds of machine learning such as previously proposed machine learning techniques based on training data associating second surgery images with particular outcomes or chances of particular outcomes, an example outcome being a complication or a lack of a complication, so as to generate a model associating image features of the first surgery image with information on a complication risk due to surgery. In some examples, the learning unit 132 updates a model by learning. For example, the learning unit 132 learns parameters of a network.

In some examples, the learning unit 132 performs a learning process using the learning data (teaching data) stored in the learning data storage unit 121, and generates a determination device (trained model). For example, the learning unit 132 generates a complication risk determination model. The learning unit 132 generates the model M1. A learning method adopted by the learning unit 132 is not specifically limited. For example, it may be possible to prepare learning data in which label information (complication risk information or the like) and a group of surgery images are associated, and perform learning by inputting the learning data to a calculation model that is based on a multi-layer neural network. For another example, it may be possible to use a method based on a deep neural network (DNN), such as a convolutional neural network (CNN) or a 3D-CNN. If time-series data, e.g., a video (moving image), such as a surgery video, is used as a target, the learning unit 132 may adopt a method based on a recurrent neural network (RNN) or a long short-term memory units (LSTM) that is an extended RNN.

For example, the learning unit 132 learns various kinds of information on the basis of information obtained from an external information processing apparatus or information stored in the storage unit 120. The learning unit 132 learns various kinds of information on the basis of information obtained from the surgery room system 5100. The learning unit 132 learns various kinds of information on the basis of information stored in the learning data storage unit 121 or the model information storage unit 122. The learning unit 132 stores a model generated by learning in the model information storage unit 122. The learning unit 132 generates the model M1 or the like.

The learning unit 132 learns various kinds of information on the basis of various kinds of information acquired by the acquiring unit 131. The learning unit 132 learns various kinds of information on the basis of various kinds of information analyzed by the analysis unit 133. The learning unit 132 learns various kinds of information on the basis of various kinds of information generated by the analysis unit 133. The learning unit 132 learns various kinds of information on the basis of various kinds of information determined by the analysis unit 133. In some examples, the learning unit 132 uses, as teaching data, the second surgery image that is a past surgery image and information on a complication risk or complication outcome due to surgery, and generates, through machine learning, a trained model as a determination model that adopts a surgery image as an input and adopts a complication risk due to surgery as an output. The learning unit 132 generates the trained model by using deep learning as the machine learning.

In some examples, the learning unit 132 performs learning by adopting a surgery image as an input and adopting a combination of information indicating a risk occurrence site and information indicating whether a risk has occurred as the correct answer information, and generates a model that outputs information on a risk occurrence site and information on the risk probability, in accordance with the input of the surgery image. For example, the learning unit 132 performs learning by adopting a surgery image as an input and adopting, as the correct answer information, a combination of information indicating a ruptured suture site and information indicating whether ruptured suture has occurred. Accordingly, in some examples, the learning unit 132 generates a model that outputs information indicating a site at which ruptured suture is likely to occur (which site location can be used in some example embodiments to identify to the system where not to superimpose warning or alert information) and a probability of the ruptured suture, in accordance with input of the surgery image. For example, the learning unit 132 performs learning by adopting a surgery image as an input and adopting, as the correct answer information, a combination of information indicating a bleeding site and information indicating whether bleeding has occurred. Accordingly, in some examples, the learning unit 132 generates a model that outputs information indicating a site at which bleeding is likely to occur and a probability of the bleeding, in accordance with input of the surgery image. For example, the learning unit 132 performs learning by adopting a surgery image as an input and adopting, as the correct answer information, a combination of information indicating a ruptured suture site and information indicating severity of ruptured suture. Accordingly, in some examples, the learning unit 132 generates a model that outputs information indicating a site at which ruptured suture is likely to occur and the severity of the ruptured suture, in accordance with input of the surgery image. For example, the learning unit 132 performs learning by adopting a surgery image as an input and adopting, as the correct answer information, a combination of information indicating a bleeding site and information indicating severity of bleeding. Accordingly, in some examples, the learning unit 132 generates a model that outputs information indicating a site at which bleeding is likely to occur and the severity of the bleeding, in accordance with input of the surgery image.

For example, the learning unit 132 learns a model by adopting information indicating occurrence of a risk in past surgery as the correct answer information and adopting a surgery image obtained before the risk becomes evident in the surgery as an input. Accordingly, in some examples, the learning unit 132 learns a model that adopts a surgery image at a first time point as an input and predicts whether a risk occurs at a second time point that is later than the first time point. In some examples, the learning unit 132 generates a trained model using learning data that includes feature information on a surgery video. In some examples, the learning unit 132 generates a trained model using learning data that includes feature information indicating at least one of a change of manipulation and a change of a surgery scene. In some examples, the learning unit 132 generates a trained model using learning data that includes feature information indicating a suture process including at least one of a suture method and a suture position.

In some examples, the learning unit 132 generates a trained model using learning data including a suture process that is detected based on a trajectory of a surgical tool (which may be detected by image analysis and/or by position and/or orientation and/or movement and/or control detectors operable with respect to the surgical tool. In some examples, the learning unit 132 generates a trained model using learning data including a suture process that is detected based on a temporal change of a position of a distal end of a surgical tool. In some examples, the learning unit 132 generates a trained model using learning data including feature information that is detected based on operating time of surgery. For example if a video (moving image), such as a surgery video, as described above is adopted as a target, the learning unit 132 generates a model based on RNN or LSTM. In some examples, the learning unit 132 generates a model using a video that includes manipulation as the feature information. In some examples, the learning unit 132 generates a model using a video that includes a change of a surgery scene as the feature information. In some examples, the learning unit 132 generates a model using a video that includes a suture process as the feature information. In some examples, the learning unit 132 generates a model using a video that includes a suture method, a suture position, or the like as the feature information.

In some examples, the learning unit 132 learns a trained model using the second surgery image that is image information including a site that becomes a cause of a surgical complication. In some examples, the learning unit 132 learns a trained model using the second surgery image that is image information including at least one of a suture site and a bleeding site.

In some examples, the learning unit 132 learns a trained model using the second surgery image that is image information including a site that is detected by image recognition. In some examples, the learning unit 132 learns a trained model using the second surgery image that is a special light observation image. In some examples, the learning unit 132 learns a trained model using the second surgery image that is an image in which an internal state of a suture site or a bleeding site is visualized.

In some examples, the learning unit 132 learns a trained model using information on a complication risk that is information indicating at least one of a probability and severity of a complication. In some examples, the learning unit 132 learns a trained model using a probability that is binary information indicating whether a complication is present or absent. In some examples, the learning unit 132 learns a trained model using severity that is five-grade information indicating a degree of impact of a complication.

In some examples, the learning unit 132 learns a trained model using information on a complication risk that is information on a risk occurrence site. In some examples, the learning unit 132 learns a trained model using information on a risk occurrence site that is information on at least one of a suture site and a bleeding site.

In some examples, the learning unit 132 may generate a model using meta-information (surgery attribute information) corresponding to a surgery image. In this case, the learning unit 132 may generate a model that adopts the surgery image and the surgery attribute information as inputs. For example, the learning unit 132 may generate a model using the surgery attribute information that includes patient information on a patient to be subjected to surgery corresponding to a surgery image. For example, the learning unit 132 may generate a model using the surgery attribute information that includes surgeon information on a surgeon who performs surgery corresponding to a surgery image.

The analysis unit 133 analyzes various kinds of information. The analysis unit 133 analyzes various kinds of information on the basis of information obtained from an external information processing apparatus or information stored in the storage unit 120. The analysis unit 133 analyzes various kinds of information on the basis of information stored in the learning data storage unit 121 or the model information storage unit 122. The analysis unit 133 identifies various kinds of information. The analysis unit 133 estimates various kinds of information.

The analysis unit 133 extracts various kinds of information. The analysis unit 133 selects various kinds of information. The analysis unit 133 extracts various kinds of information on the basis of information obtained from an external information processing apparatus or information stored in the storage unit 120. The analysis unit 133 extracts various kinds of information from the storage unit 120. The analysis unit 133 extracts various kinds of information from the learning data storage unit 121 or the model information storage unit 122.

The analysis unit 133 extracts various kinds of information on the basis of various kinds of information acquired by the acquiring unit 131. The analysis unit 133 extracts various kinds of information on the basis of information generated by the analysis unit 133. Further, the analysis unit 133 extracts various kinds of information on the basis of various kinds of information determined by the analysis unit 133. The analysis unit 133 extracts various kinds of information on the basis of various kinds of information learned by the learning unit 132.

The analysis unit 133 generates various kinds of information. The analysis unit 133 generates various kinds of information on the basis of information obtained from an external information processing apparatus or information stored in the storage unit 120. The analysis unit 133 generates various kinds of information on the basis of information obtained from the surgery room system 5100. The analysis unit 133 generates various kinds of information on the basis of information stored in the learning data storage unit 121 or the model information storage unit 122.

The analysis unit 133 determines various kinds of information. The analysis unit 133 performs various kinds of determination. For example, the analysis unit 133 determines various kinds of information on the basis of information obtained from an external information processing apparatus or information stored in the storage unit 120. The analysis unit 133 determines various kinds of information on the basis of information obtained from the surgery room system 5100. The analysis unit 133 determines various kinds of information on the basis of information stored in the learning data storage unit 121 or the model information storage unit 122.

The analysis unit 133 generates risk analysis information on the first surgery image by applying the first surgery image to a trained model that is generated using learning data including the second surgery image that is a surgery image different from the first surgery image and including (or having associated) information on a complication risk due to surgery.

The analysis unit 133 generates risk analysis information indicating a complication risk due to first surgery corresponding to the first surgery image. The analysis unit 133 generates the risk analysis information by inputting the first surgery image to the trained model acquired by the acquiring unit 131. If a model that outputs information indicating a risk occurrence site in accordance with an input is used, the analysis unit 133 generates the risk analysis information including information on the risk occurrence site by using the output of the model. For example, if a model that outputs information indicating a ruptured suture site and a probability of ruptured suture is used, the analysis unit 133 generates the risk analysis information indicating a site at which ruptured suture is likely to occur and a probability of the ruptured suture by using the output of the model. For example, if a model that outputs information indicating a bleeding site and a probability of bleeding is used, the analysis unit 133 generates the risk analysis information indicating a site at which bleeding is likely to occur and a probability of the bleeding by using the output of the model. For example, if a model that outputs information indicating a ruptured suture site and severity of ruptured suture is used, the analysis unit 133 generates the risk analysis information indicating a site at which ruptured suture is likely to occur and severity of the ruptured suture by using the output of the model. For example, if a model that outputs information indicating a bleeding site and severity of bleeding is used, the analysis unit 133 generates the risk analysis information indicating a site at which bleeding is likely to occur and severity of the bleeding by using the output of the model.

The analysis unit 133 generates the risk analysis information by using the first surgery image that is high-quality low-latency image information that meets an image quality condition on image quality and a latency condition on latency. The analysis unit 133 generates the risk analysis information by using the first surgery image that is image information with resolution of 4K or higher, which is an example of a "high quality" image meeting an image quality condition of 4K resolution or higher. An example of a "low latency" image is an image with a latency (capture to display) meeting an image latency condition of a latency of no more than 20 milliseconds, preferably a few milliseconds, more preferably 1 millisecond. The analysis unit 133 generates the risk analysis information by using the first surgery image that is a special light observation image.

The analysis unit 133 generates the risk analysis information by using the trained model that is generated using the second surgery image that is image information including a site that becomes a cause of a surgical complication (and which may be associated with information indicating such a complication risk). The analysis unit 133 generates the risk analysis information by using the trained model that is generated using the second surgery image that is image information including at least one of a suture site and a bleeding site.

Note that the information associated with the second surgery image and indicative of a complication risk can be "100%" in that a complication did in fact occur in the surgery represented by that second surgery information, or may be "0%" if a complication did not occur in the surgery represented by that second surgery information.

In some examples, the analysis unit 133 generates the risk analysis information by using the trained model that is generated using the second surgery image that is image information including a site that is detected by image recognition. In some examples, the analysis unit 133 generates the risk analysis information by using the trained model that is generated using the second surgery image that is a special light observation image. In some examples, the analysis unit 133 generates the risk analysis information by using the trained model that is generated using the second surgery image that is an image in which an internal state of a suture site or a bleeding site is visualized.

In some examples, the analysis unit 133 generates the risk analysis information by using the trained model that is generated using information on a complication risk that is information indicating at least one of a probability and severity of a complication. In some examples, the analysis unit 133 generates the risk analysis information by using the trained model that is generated using the probability that is binary information indicating whether the complication is present or absent. In some examples, the analysis unit 133 generates the risk analysis information by using the trained model that is generated using the severity that is five-grade information indicating a degree of impact of the complication.

In some examples, the analysis unit 133 generates the risk analysis information by using the trained model that is generated using the information on the complication risk that is information on a risk occurrence site. In some examples, the analysis unit 133 generates the risk analysis information by using the trained model that is generated using the information on the risk occurrence site that is information on at least one of a suture site and a bleeding site.

In some examples, the analysis unit 133 generates the risk analysis information by adopting the first surgery image subjected to a correction process to the trained model. In some examples, the analysis unit 133 generates the risk analysis information by adopting the first surgery image subjected to a correction process that is a process related to at least one of rotation, distortion, and resolution.

In some examples, the analysis unit 133 generates the risk analysis information that is information including at least one of a probability and severity of a complication risk. In some examples, the analysis unit 133 generates the risk analysis information including information on a risk occurrence site. In some examples, the analysis unit 133 generates the risk analysis information that is information including information on at least one of a ruptured suture site and a bleeding site and including at least one of a probability and severity of a complication risk at the site.

In some examples, the analysis unit 133 executes predetermined processes in risk analysis by using a cloud server. In some examples, the analysis unit 133 generates the risk analysis information that is information in which information having a trade-off relationship with a complication is taken into account. In some examples, the analysis unit 133 generates the risk analysis information that is information in which information having a trade-off relationship with ruptured suture is taken into account. In some examples, the analysis unit 133 generates the risk analysis information that is information in which surgery duration having a trade-off relationship with ruptured suture is taken into account. If the surgery duration exceeds a predetermined threshold, in some examples, the analysis unit 133 determines that surgery support information is not to be output. If the surgery duration exceeds a predetermined threshold due to output of the surgery support information, in some examples, the analysis unit 133 determines that the surgery support information is not to be output. If expected surgery duration exceeds a predetermined threshold, in some examples, the analysis unit 133 determines that the surgery support information is not to be output.

In some examples, the analysis unit 133 generates the surgery support information based on the risk analysis information. In some examples, the analysis unit 133 generates the surgery support information that is information indicating a position of a risk site. For example, when a model that outputs information indicating a ruptured suture site and a probability of ruptured suture is used, and if the probability output by the model is equal to or higher than a predetermined threshold (for example, 70% or the like), In some examples, the analysis unit 133 generates the surgery support information indicating the ruptured suture site that is output by the model. For example, when a model that outputs information indicating a bleeding site and a probability of bleeding is used, and if the probability output by the model is equal to or higher than a predetermined threshold (for example, 75% or the like), the analysis unit 133 generates the surgery support information indicating the bleeding site that is output by the model. For example, when a model that outputs information indicating a ruptured suture site and severity of ruptured suture is used, and if the severity output by the model is equal to or higher than a predetermined threshold (for example, fourth grade or higher), In some examples, the analysis unit 133 generates the surgery support information indicating the ruptured suture site that is output by the model. For example, when a model that outputs information indicating a bleeding site and severity of bleeding is used, and if the severity output by the model is equal to or higher than a predetermined threshold (for example, third grade or higher), the analysis unit 133 generates the surgery support information indicating the bleeding site that is output by the model.

In some examples, the analysis unit 133 generates the surgery support information that is superimposed on a position that does not overlap with the risk site. In some examples, the analysis unit 133 generates the surgery support information that is information indicating at least one of a probability and severity of a risk. In some examples, the analysis unit 133 generates the surgery support information with a predetermined shape or color.

In some examples, the analysis unit 133 generates the surgery support information for which the shape or the color is changed in accordance with at least one of a probability and severity of a risk. In some examples, the analysis unit 133 generates the surgery support information that is subjected to at least one of movement and blinking on the surgery image. In some examples, the analysis unit 133 generates the surgery support information for which at least one of a moving speed and motion is controlled in accordance with at least one of a probability and severity of a risk.

In some examples, the analysis unit 133 generates the surgery support information for which content is dynamically changed on the basis of at least one of surgery duration and a surgery scene. In some examples, the analysis unit 133 generates the surgery support information for which display is controlled based on a predetermined criterion. In some examples, the analysis unit 133 generates the surgery support information that is displayed after a lapse of a predetermined period since notice is given by voice. In some examples, the analysis unit 133 generates the surgery support information that is displayed for a predetermined period during surgery.

In the case of a special light observation image, in some examples, the analysis unit 133 generates the surgery support information that is displayed in a predetermined mode. In some examples, the analysis unit 133 generates the risk analysis information for surgery for which a surgery difficulty level varies depending on a disease, a site, or a surgery procedure. In some examples, the analysis unit 133 generates the risk analysis information by analyzing an external state of suture using normal light and analyzing an internal state of the suture using special light.

In some examples, the analysis unit 133 may identify a risk site. In some examples, the analysis unit 133 may identify a risk site by appropriately using various conventional techniques, such as image recognition. When a certain surgery image is input to a risk occurrence determination model and the determination model outputs a score equal to or higher than a predetermined threshold, in some examples, the analysis unit 133 may identify a risk site in the certain surgery image by performing image analysis on the certain surgery image.

In some examples, the analysis unit 133 may generate various kinds of information, such as a screen (image information), to be provided to an external information processing apparatus, by appropriately using various techniques. In some examples, the analysis unit 133 may generate various kinds of information, such as a screen (image information), to be provided to an output unit. In some examples, the analysis unit 133 generates a screen (image information) or the like to be provided to the surgery room system 5100. For example, the analysis unit 133 generates a screen (image information) or the like to be provided to the surgery room system 5100 on the basis of information stored in the storage unit 120. In some examples, the analysis unit 133 may generate a screen (image information) or the like by any process as long as it is possible to generate the screen (image information) to be provided to an external information processing apparatus. For example, the analysis unit 133 generates a screen (image information) to be provided to the surgery room system 5100 by appropriately using various techniques related to image formation, image processing, or the like. For example, the analysis unit 133 generates a screen (image information) to be provided to the surgery room system 5100 by appropriately using various techniques, such as Java (registered trademark). Meanwhile, in some examples, the analysis unit 133 may generate a screen (image information) to be provided to the surgery room system 5100 based on a format of CSS, JavaScript (registered trademark), or HTML. Further, for example, the analysis unit 133 may generate a screen (image information) in various formats, such as joint photographic expert group (JPEG), graphics interchange format (GIF), or portable network graphics (PNG).

The transmitting unit 134 provides various kinds of information to an external information processing apparatus. The transmitting unit 134 transmits various kinds of information to an external information processing apparatus. For example, the transmitting unit 134 transmits various kinds of information to the surgery room system 5100. The transmitting unit 134 provides information stored in the storage unit 120. The transmitting unit 134 transmits information stored in the storage unit 120.

The transmitting unit 134 provides various kinds of information on the basis of information obtained from the surgery room system 5100. The transmitting unit 134 provides various kinds of information on the basis of information stored in the storage unit 120. The transmitting unit 134 provides various kinds of information on the basis of information stored in the learning data storage unit 121 or the model information storage unit 122.

The transmitting unit 134 transmits the surgery support information based on the risk analysis information. The transmitting unit 134 transmits the surgery support information based on the risk analysis information. The transmitting unit 134 transmits the surgery support information that is information indicating a position of a risk site. The transmitting unit 134 transmits the surgery support information that is superimposed on a position that does not overlap with the risk site. The transmitting unit 134 transmits the surgery support information that is information indicating at least one of a probability and severity of a risk.

The transmitting unit 134 transmits the surgery support information with a predetermined shape or color. The transmitting unit 134 transmits the surgery support information for which the shape or the color is changed in accordance with at least one of a probability and severity of a risk. The transmitting unit 134 transmits the surgery support information for which at least one of movement and blinking is performed on the surgery image.

The transmitting unit 134 transmits the surgery support information for which at least one of a moving speed and motion is controlled in accordance with at least one of a probability and severity of a risk. The transmitting unit 134 transmits the surgery support information for which content is dynamically changed on the basis of at least one of surgery duration and a surgery scene.

The transmitting unit 134 transmits the surgery support information for which display is controlled based on a predetermined criterion. The transmitting unit 134 transmits the surgery support information that is displayed after a lapse of a predetermined period since notice is given by voice. The transmitting unit 134 transmits the surgery support information that is displayed for a predetermined period during surgery. In the case of a special light observation image, the transmitting unit 134 transmits the surgery support information that is displayed in a predetermined mode.

<3-2. Example of Output Apparatus According to Embodiment>

An example of the output apparatus according to the embodiment will be described below. In the example as described above, the display apparatus 5155 of the surgery room system 5100 serves as an output apparatus that functions as an output unit that outputs the surgery support information that is based on the risk analysis information generated by the information processing apparatus 100. For example, the display apparatus 5155 includes a liquid crystal display, an organic electro-luminescence (EL) display, or the like. The display apparatus 5155 displays various kinds of information. The display apparatus 5155 displays information acquired from the information processing apparatus 100 and information acquired from various apparatuses of the surgery room system 5100. The display apparatus 5155 displays the surgery support information acquired from the information processing apparatus 100 and surgery images acquired from the various apparatuses of the surgery room system 5100.

The display apparatus 5155 functions as an output apparatus (output unit). The display apparatus 5155 outputs the surgery support information that is based on the risk analysis information generated by the analysis unit 133, in a superimposed manner on the surgery image. The display apparatus 5155 outputs the surgery support information that is based on the risk analysis information, in a superimposed manner on the surgery image of the first surgery.

The display apparatus 5155 outputs the surgery support information that is information indicating a position of a risk site, in a superimposed manner on the surgery image of the first surgery. The display apparatus 5155 outputs the surgery support information that is superimposed on a position that does not overlap with the risk site, in a superimposed manner on the surgery image of the first surgery. The display apparatus 5155 outputs, in a superimposed manner, the surgery support information at a position that does not overlap with a risk site in the surgery image of the first surgery.

The display apparatus 5155 outputs the surgery support information that is information indicating at least one of a probability and severity of a risk, in a superimposed manner on the surgery image of the first surgery. The display apparatus 5155 outputs the surgery support information with a predetermined shape or color, in a superimposed manner on the surgery image of the first surgery.

The display apparatus 5155 outputs the surgery support information for which the shape or the color is changed in accordance with at least one of a probability and severity of a risk, in a superimposed manner on the surgery image of the first surgery. The display apparatus 5155 outputs the surgery support information for which at least one of movement and blinking is performed on the surgery image, in a superimposed manner on the surgery image of the first surgery.

The display apparatus 5155 outputs the surgery support information for which at least one of a moving speed and motion is controlled in accordance with at least one of a probability and severity of a risk, in a superimposed manner on the surgery image of the first surgery. The display apparatus 5155 outputs the surgery support information for which content is dynamically changed on the basis of at least one of surgery duration and a surgery scene, in a superimposed manner on the surgery image of the first surgery.

The display apparatus 5155 outputs the surgery support information for which display is controlled based on a predetermined criterion, in a superimposed manner on the surgery image of the first surgery. The display apparatus 5155 outputs the surgery support information that is displayed after a lapse of a predetermined period since notice is given by voice, in a superimposed manner on the surgery image of the first surgery.

The display apparatus 5155 outputs the surgery support information that is displayed for a predetermined period during surgery, in a superimposed manner on the surgery image of the first surgery. The display apparatus 5155 outputs the surgery support information for a predetermined period during surgery, in a superimposed manner on the surgery image of the first surgery.

In the case of a special light observation image, the display apparatus 5155 outputs the surgery support information that is displayed in a predetermined mode, in a superimposed manner on the surgery image of the first surgery. In the case of a special light observation image, the display apparatus 5155 outputs the surgery support information in a predetermined mode, in a superimposed manner on the surgery image of the first surgery.

The output apparatus may be any apparatus, such as the display apparatuses 5103A to 5103D or the centralized operation panel 5111.

<3-3. Procedure of Surgery Support Process According to Embodiment>

A flow of various surgery support processes according to the embodiment will be described below with reference to FIG. 8. FIG. 8 is a flowchart illustrating the flow of the surgery support process according to the embodiment of the present disclosure. A process at each of steps may be performed by any apparatus, such as the information processing apparatus 100 or each of the apparatuses of the surgery room system 5100, included in the surgery support system 1.

As illustrated in FIG. 8, the surgery support system 1 acquires the first surgery image (Step S101). For example, the information processing apparatus 100 acquires the first surgery image. For example, the information processing apparatus 100 acquires the first surgery image that is captured in the surgery room system 5100 in which surgery is performed.

The surgery support system 1 generates the risk analysis information on the surgery image by applying the first surgery image to a trained model that is generated using learning data including both of the second surgery image and information on a complication risk due to surgery (Step S102). For example, the information processing apparatus 100 generates the risk analysis information on the surgery image by applying the first surgery image to the learned trained model. For example, the information processing apparatus 100 generates the risk analysis information on the surgery image by applying the first surgery image to the model M1 that is the trained model stored in the model information storage unit 122 (see FIG. 7).

The surgery support system 1 outputs the surgery support information that is based on the analysis information, in a superimposed manner on the surgery image (Step S103). For example, the information processing apparatus 100 generates the surgery support information based on the analysis information, and transmits the surgery support information to the surgery room system 5100. The surgery room system 5100 that has received the surgery support information outputs the surgery support information in a superimposed manner on the surgery image. The display apparatus 5155 of the surgery room system 5100 displays the surgery support information in a superimposed manner on the surgery image.

<3-4. Overview of Surgery Support Process According to Embodiment>

Figure 9:
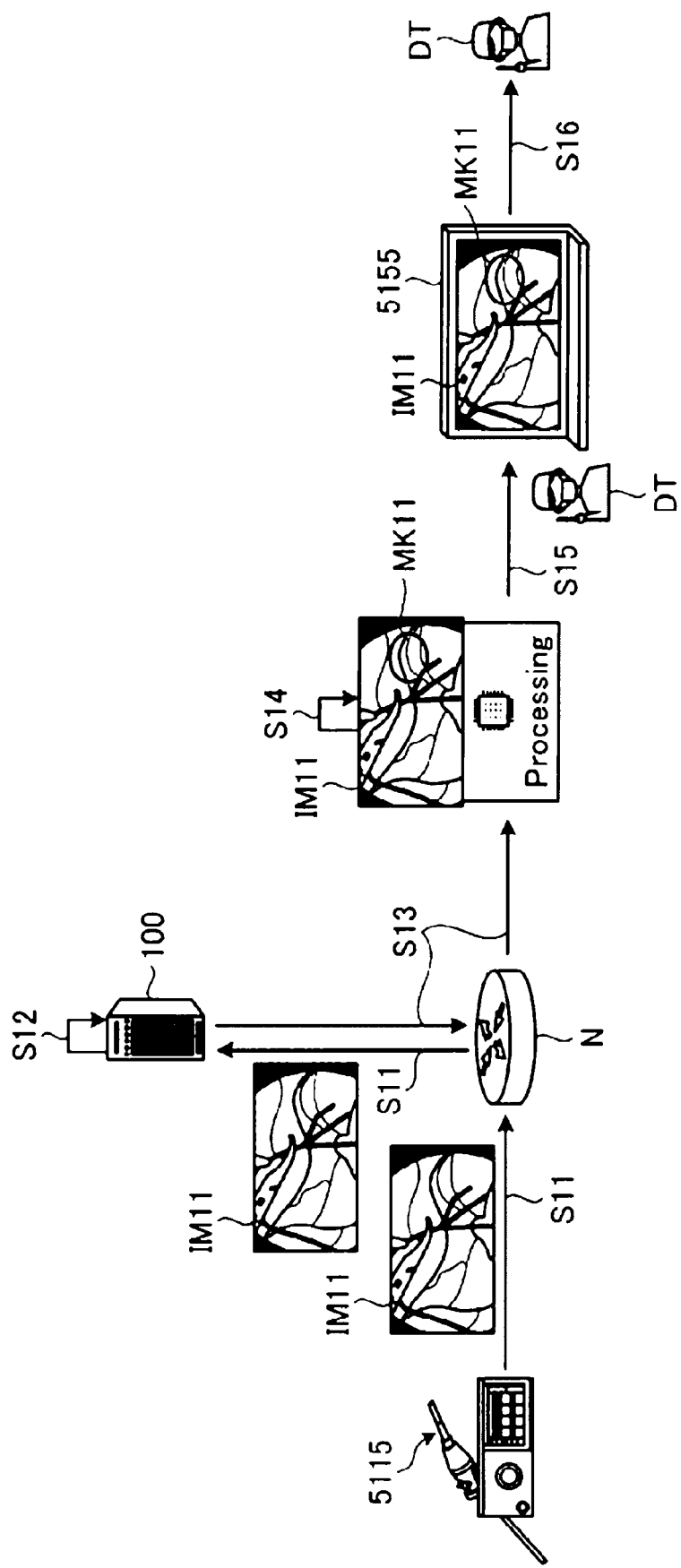
FIG. 9 is a diagram illustrating an example of the surgery support process according to the embodiment of the present disclosure.

FIG. 9 is a diagram illustrating an example of the surgery support process according to the embodiment of the present disclosure. Information processing according to the embodiment of the present disclosure is realized by the constituent elements included in the surgery support system 1 as described above.

First, the information processing apparatus 100 acquires a surgery image IM11 as the first surgery image (Step S11). For example, a scopist operates a rigid endoscope and captures a video while a surgeon performs suture. In the example illustrated in FIG. 9, the information processing apparatus 100 acquires the surgery image IM11 that is captured by the endoscope 5115 of the surgery room system 5100. The information processing apparatus 100 acquires the surgery image IM11 from the surgery room system 5100 via the network N. A communication apparatus CM (for example, the CCU 5153 or the like) that is included in the surgery room system 5100 and that has a communication function transmits the surgery image IM11 to the information processing apparatus 100 via the network N. The communication apparatus CM acquires the surgery image IM11 captured by the endoscope 5115, and transmits the surgery image IM11 to the information processing apparatus 100. The communication apparatus CM acquires the surgery image IM11 from the endoscopic surgery system 5113, and transmits the surgery image IM11 to the information processing apparatus 100. While only the surgery image IM11 is illustrated in the example in FIG. 9, the surgery image may be a surgery video. In this case, the surgery video is transferred from the surgery room system 5100 to the information processing apparatus 100 via the network N.

Then, the information processing apparatus 100 performs an analysis process (Step S12). For example, the surgery support system 1 performs the analysis process using cloud AI or server analysis. In the example illustrated in FIG. 9, the information processing apparatus 100 performs the analysis process using the surgery image IM11. For example, the information processing apparatus 100 may perform the analysis process using a trained database with annotation for a risk of ruptured suture and a portion of ruptured suture. The information processing apparatus 100 may perform the analysis process by appropriately using a technique of recognition analysis, morphological analysis, or the like. For example, the information processing apparatus 100 may perform the analysis process including determination of a risk of ruptured suture.

The information processing apparatus 100 performs the analysis process by applying the surgery image IM11 to the model M1. The information processing apparatus 100 inputs the surgery image IM11 to the model M1, and performs the analysis process using information output from the model M1. The information processing apparatus 100 performs the analysis process using information indicating a risk probability or information indicating a risk occurrence site, where the information is output by the model M1 to which the surgery image IM11 has been input.

The information processing apparatus 100 determines that a risk is present if the information indicating the risk probability, which is output by the model M1 to which the surgery image IM11 has been input, is equal to or larger than a predetermined threshold. Further, the information processing apparatus 100 determines that a risk is absent if the information indicating the risk probability, which is output by the model M1 to which the surgery image IM11 has been input, is smaller than a predetermined threshold. Then, the information processing apparatus 100 generates risk determination information indicating a determination result. The information processing apparatus 100 generates high-risk position information using the information indicating the risk occurrence site, which is output by the model M1 to which the surgery image IM11 has been input. In the example illustrated in FIG. 9, the information processing apparatus 100 generates the risk determination information indicating that it is determined that a risk is present, and generates information indicating that a risk occurrence site is located in a right-center portion in the surgery image IM11. Specifically, the information processing apparatus 100 generates information indicating that the risk occurrence site is a region that is located inside a mark MK11 in the surgery image IM11.

Then, the information processing apparatus 100 transmits the generated risk determination information or the generated high-risk position information to the surgery room system 5100 (Step S13). The generated risk determination information or the generated high-risk position information is transmitted to an apparatus that has a communication function in the surgery room system 5100. For example, the CCU 5153 of the surgery room system 5100 (see FIG. 3) transmits and receives information to and from the information processing apparatus 100 via the network N. Further, the CCU 5153 may transmit and receive information to and from the information processing apparatus 100 via a different apparatus (the communication apparatus CM) or the like that has a communication function in the surgery room system 5100. The CCU 5153 acquires the risk determination information or the high-risk position information generated by the information processing apparatus 100.

The CCU 5153 performs image processing using the risk determination information or the high-risk position information (Step S14). The CCU 5153 performs image processing (signal processing) of superimposing information on an image, or the like. For example, the CCU 5153 superimposes a determination result on a high-quality low-latency video. In the example illustrated in FIG. 9, the CCU 5153 superimposes the surgery support information indicating that the risk occurrence site is located in the right-center portion in the surgery image IM11 on the surgery image IM11. Specifically, the CCU 5153 superimposes, as the surgery support information, a ring-shape mark MK11, which encloses a region that is determined as the risk occurrence site in the surgery image IM11, onto the surgery image IM11. In this manner, the mark MK11 is superimposed such that a risk site is enclosed in the surgery image IM11. In other words, the mark MK11 is superimposed on a position that does not overlap with the risk site in the surgery image IM11.

Then, the CCU 5153 causes the display apparatus 5155 to display the surgery image IM11 on which the mark MK11 is superimposed as the surgery support information (Step S15). The CCU 5153 transmits the surgery image IM11 on which the mark MK11 is superimposed as the surgery support information to the display apparatus 5155, and causes the display apparatus 5155 to display the surgery image IM11 on which the mark MK11 is superimposed. The display apparatus 5155 that has received the surgery image IM11 on which the mark MK11 is superimposed from the CCU 5153 displays the surgery image IM11 on which the mark MK11 is superimposed. Accordingly, a medical professional DT, such as a surgeon (doctor), checks the surgery image IM11 on which the mark MK11 is superimposed.

The medical professional DT that has checked the information displayed on the display apparatus 5155 performs treatment, such as resuture, on the basis of contents of the information (Step S16). Therefore, the surgery support system 1 can reduce a complication of ruptured suture.

In the example in FIG. 9, the case has been described in which the surgery image (high-resolution image or the like) is transmitted from the surgery room system 5100 to the information processing apparatus 100; however, the surgery support system 1 may perform processes as described below. For example, the surgery support system 1 may cause the surgery room system 5100 to detect a landmark (a suture site, a bleeding site, a thread, or the like) of an affected area. In this case, the surgery support system 1 detects the landmark of the affected area as described above, by using a multi-layer image sensor of the surgery room system 5100 and using signal processing in the sensor. Then, the surgery support system 1 transmits only a detection result (instead of a high-resolution image) from the surgery room system 5100 to a server (the information processing apparatus 100) via a mobile industry processor interface (MIPI), and causes the cloud server (the information processing apparatus 100) to perform a recognition process.

With this configuration, it is possible to avoid load centralization on the server and reduce a transmission data volume in the surgery support system 1. For example, by causing the surgery room system 5100 to detect the landmark of the affected area, the surgery support system 1 is able to avoid load centralization in the server (the information processing apparatus 100). Further, by transmitting the detection result of the landmark of the affected area instead of the high-resolution image (the surgery image or the like) from the surgery room system 5100 to the information processing apparatus 100, the surgery support system 1 is able to reduce a volume of data transferred to the server (the information processing apparatus 100). Furthermore, in this case, the surgery support system 1 causes the server to generate the surgery support information, transmit the surgery support information to a client site, and display the surgery support information in a superimposed manner at the client site. For example, the information processing apparatus 100 generates the surgery support information based on the acquired detection result of the landmark of the affected area, and transmits the surgery support information to the surgery room system 5100. The surgery room system 5100 that has received the surgery support information causes the display apparatus 5155 or the like to display the surgery support information in a superimposed manner on the surgery image.

<3-5. Output Example of Surgery Support Information>

The surgery support system 1 may output the surgery support information in any mode as long as the surgery support information is output in a superimposed manner on the surgery image. This will be described below with reference to FIG. 10 and FIG. 11.

<3-5-1. Display of Surgery Support Information>

Figure 10:
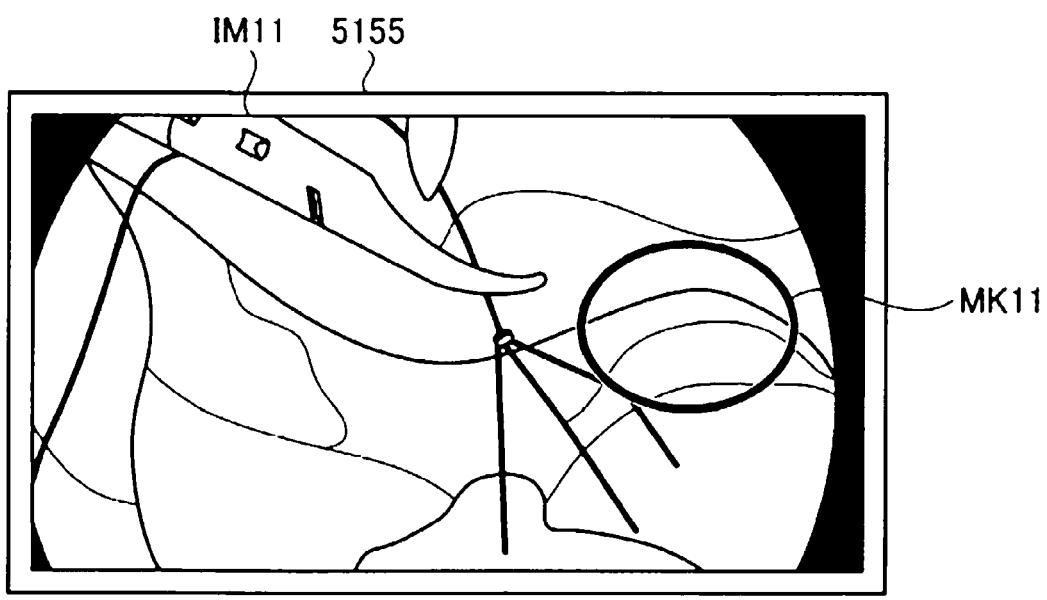
FIG. 10 is a diagram illustrating an example of output of surgery support information.

First, display of the surgery support information will be described with reference to FIG. 10. FIG. 10 is a diagram illustrating an example of output of the surgery support information.

In the example illustrated in FIG. 10, the display apparatus 5155 displays the surgery image IMI1 on which the mark MK11 is superimposed. The display apparatus 5155 displays the surgery support information indicating that the risk occurrence site is located in a right-center portion in the surgery image IM11, in a superimposed manner on the surgery image IM11. Specifically, the display apparatus 5155 displays the ring-shape mark MK11, which encloses a region that is determined as the risk occurrence site in the surgery image IM11, in a superimposed manner on the surgery image IM11. In this manner, the display apparatus 5155 displays the surgery support information at a position related to the risk site.

The display illustrated in FIG. 10 is one example. The way of displaying the surgery support information in a superimposed manner on the surgery image by the surgery support system 1 may be arbitrary. The display apparatus 5155 may display the surgery support information in a picture-in-picture (PinP) manner. For example, the display apparatus 5155 displays an image (sub image) that is obtained by superimposing the surgery support information on the surgery image IM1, separately from the surgery image IM11 (main image). The display apparatus 5155 displays the surgery image IMI1 as the main image with a maximum size, and displays the sub image on which the surgery support information is superimposed with a smaller size than that of the main image. With this configuration, a medical professional can clearly view a treatment portion in the main image without being disturbed by the surgery support information, and also can check a risk portion using the sub image.

For example, the surgery support system 1 may superimpose the surgery support information on a position that is less likely to disturb surgery in the surgery image. For example, the surgery support system 1 may display the surgery support information that represents the risk site with text (language) in black regions at four corners of the surgery image IM11. The surgery support system 1 may display, as the surgery support information, textual information, such as "risk present in right-center portion" in the upper right black region in the surgery image IM11.

The surgery support system 1 need not always display the ring-shape mark M11 as illustrated in FIG. 10, but may display various kinds of surgery support information, such as a translucent mark. Further, the surgery support system 1 may display, as the surgery support information, a mark for which a color or a size is changed depending on a risk. For example, the surgery support system 1 may display, as the surgery support information, a mark for which a color is changed from cold colors to warm colors depending on a risk. For example, the surgery support system 1 may display, as the surgery support information, a mark that is displayed in blue when a risk is low and that is displayed in red when a risk is high. For example, the surgery support system 1 may display, as the surgery support information, a mark for which a size is increased with an increase in a risk. For example, the surgery support system 1 may display a suture site in different colors depending on risks.

Further, the surgery support system 1 may change a display mode on the basis of various kinds of information. The surgery support system 1 may change the display mode on the basis of the surgery attribute information. The surgery support system 1 may change the display mode in accordance with details of surgery. The surgery support system 1 may change the display mode in accordance with a surgery difficulty level. For example, the surgery support system 1 may display more detailed information with an increase in the surgery difficulty level.

The surgery support system 1 may change display depending on a surgeon. The surgery support system 1 may change the display mode on the basis of the surgeon information. The surgery support system 1 may reduce the number of times of display or an amount of information for a surgeon having a longer carrier.

<3-5-2. Two-Step Output>

Figure 11:
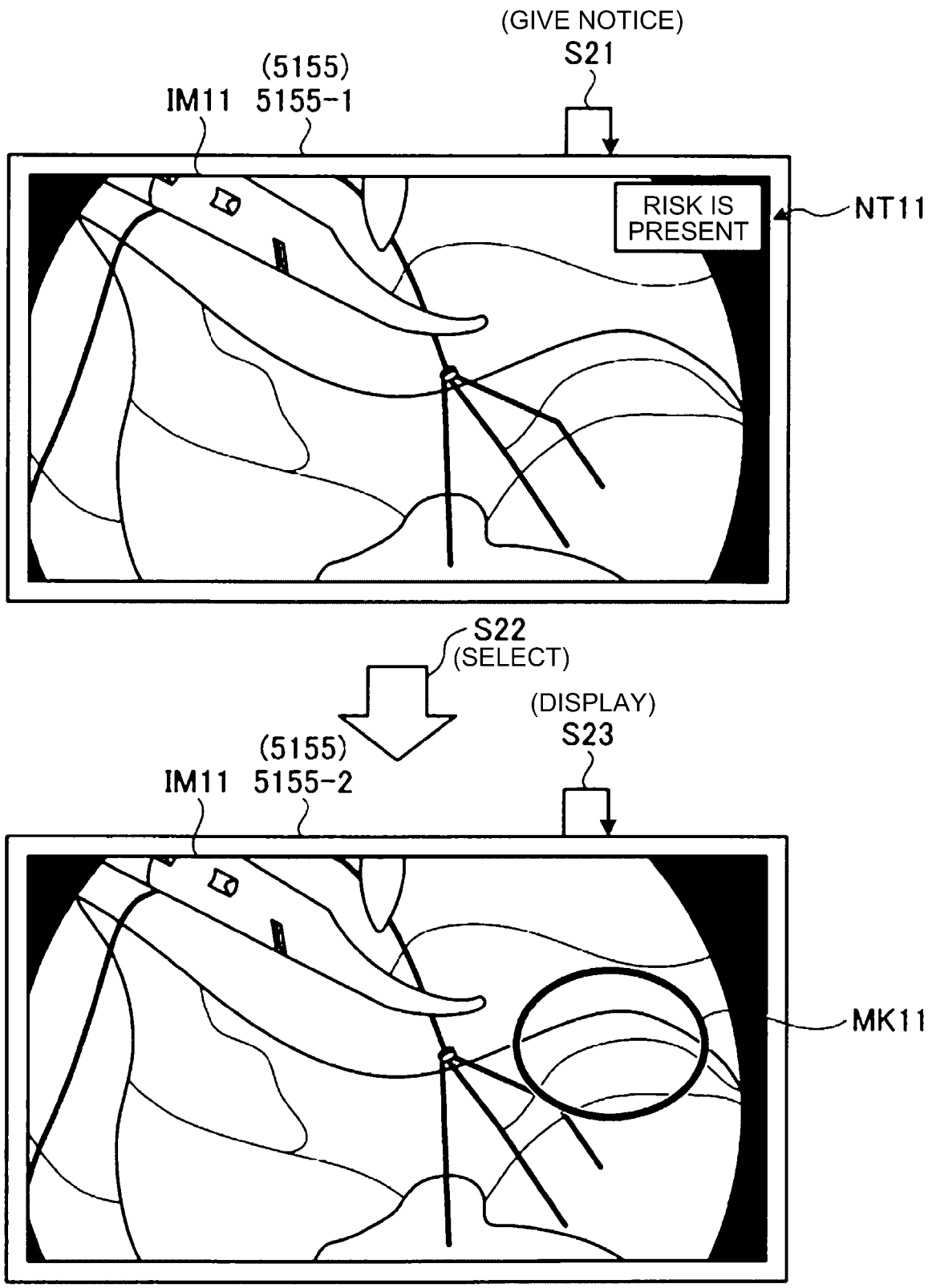
FIG. 11 is a diagram illustrating another example of output of the surgery support information.

Two-step output will be described below with reference to FIG. 11. FIG. 11 is a diagram illustrating another example of the output of the surgery support information. In the example illustrated in FIG. 11, two-step display will be described as one example of the two-step output, but various output modes may be adopted as long as output is performed in a two-step manner. For example, it may be possible to give notice by voice at an initial step (first step), and it may be possible to perform display at a next step (second step) if a response is given to the notice. In this case, it may be possible to give notice, such as "there is a risk, do you want to display the risk?", by voice at the first step, and display a mark or the like in a superimposed manner on a surgery image at the second step if the surgeon gives permission to perform display. In this manner, it may be possible to adopt different output modes at different steps, such as using voice at the first step and performing display at the second step.

The example illustrated in FIG. 11 will be described using a display apparatus 5155-1 that corresponds to a display mode at the first step and a display apparatus 5155-2 using a display mode at the second step. The display apparatus 5155-1 and the display apparatus 5155-2 are the same display apparatuses 5155, and will be described as the display apparatuses 5155 when they need not be specifically distinguished from each other.

If it is determined that a risk is present, the surgery support system 1 gives notice indicating that a risk is present as the first step (Step S21). The display apparatus 5155-1 displays character information NT11 of "risk is present" in an upper right region in the surgery image IM11, to thereby notify (give notice) the surgeon that the risk is present.

The surgeon who has notified (received the notice) that the risk is present selects display of details of the risk (Step S22). For example, the surgeon selects display of details of the risk by voice saying "display details" or by predetermined operation.

Then, the surgery support system 1 displays, as the second step, the details of the risk (Step S23). The display apparatus 5155-2 displays the mark MK11 in a superimposed manner on the surgery image IM11. The display apparatus 5155 displays the surgery support information indicating that the risk occurrence site is located in the right-center portion in the surgery image IM11, in a superimposed manner on the surgery image IM11. If the surgeon does not select output for the second step, the surgery support system 1 does not perform output at the second step.

In this manner, the surgery support system 1 performs output in a two-step manner, and performs output at the second step when the surgeon gives permission at the first step, so that it is possible to output the surgery support information in a superimposed manner on the surgery image without disturbing the surgeon.

<3-6. Example of Process Performed by Surgery Support System>

Figure 12:
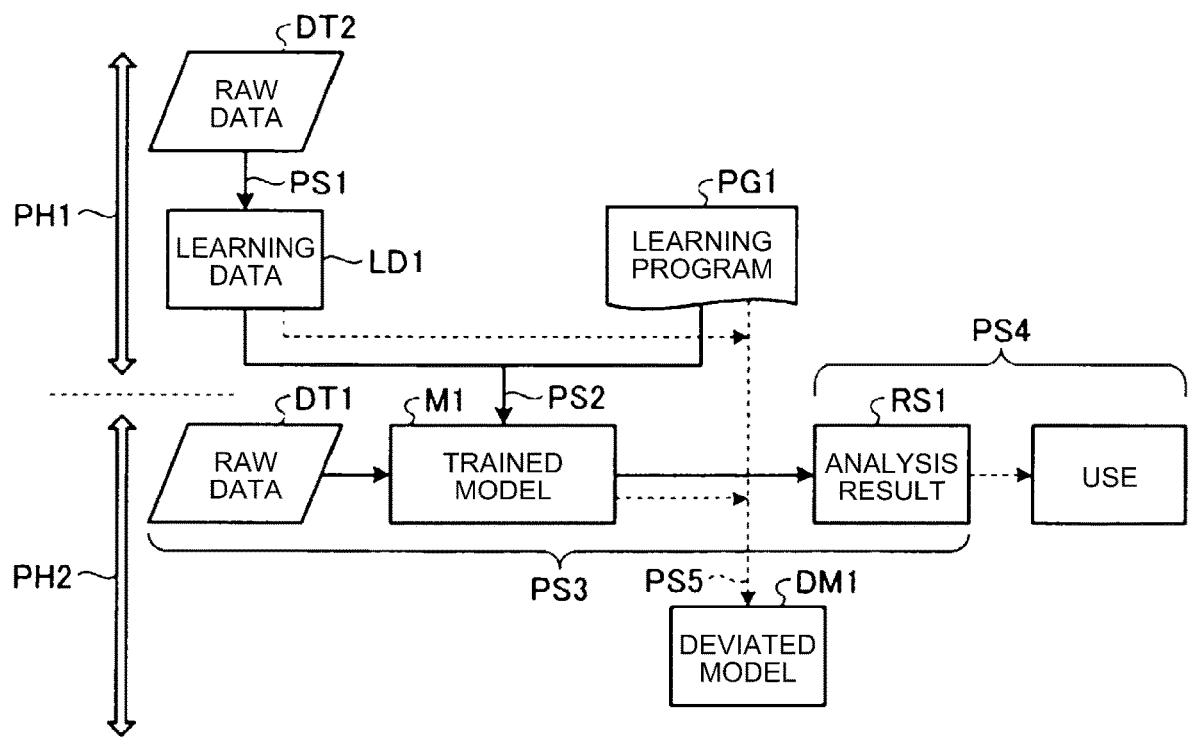
FIG. 12 is a diagram illustrating an example of a process performed by the surgery support system.

A process performed by the surgery support system will be conceptually described below with reference to FIG. 12. FIG. 12 is a diagram illustrating an example of the process performed by the surgery support system. For example, the process illustrated in FIG. 12 is executed by the surgery support system 1.

The example of the process performed by the surgery support system as illustrated in FIG. 12 includes a learning phase PH1 for generating artificial intelligence (AI) and a use phase PH2 for using the AI. The process performed by the surgery support system need not always be performed such that the learning phase PH1 is first performed and thereafter the use phase PH2 is performed. In the process performed by the surgery support system, it may be possible to perform the learning phase PH1 and the use phase PH2 in parallel, and repeatedly update (modify) a trained model by using a trained model. The entire process including the learning phase PH1 and the use phase PH2 corresponds to the entire process using the AI.

Raw data DT2 illustrated in FIG. 12 corresponds to the second surgery image. A process PS1 for generating learning data LD1 using the raw data DT2 that is the second surgery image is performed. The learning data LD1 includes a surgery video (surgery image), a site, a complication risk indicating a grade (severity or the like), and the like. A learning program PG1 may include information indicating a learning method to be used. The learning program PG1 may include information indicating a learning method to be used, such as supervised learning or unsupervised learning. The learning program PG1 may include a learning algorithm or the like.

Through a learning process PS2 using the learning data LD1 and the learning program PG1, the model M1 that is a trained model is generated.

The raw data DT1 illustrated in FIG. 12 corresponds to the first surgery image. By adopting the row data DT1 as the first surgery image to the model M1 that is the trained model, a process PS3 for generating an analysis result is performed. For example, through the process PS3, a function for classification or the like is implemented. By inputting the raw data DT1 to the model M1, an analysis result RS1 is generated using information output by the model M1. The analysis result RS1 corresponds to the risk analysis information, a risk, or the surgery support information indicating a risk site. Then, a process PS4 using the analysis result RS1 is performed. For example, the analysis result RS1 is used by outputting the information to the surgeon such that the surgery support information is output in a superimposed manner on the raw data DT1. The use of the analysis result RS1 may be various kinds of information display methods.

Further, it may be possible to generate a derived model DM1 through a learning process PS5 using the model M1 that is the trained model, the learning data LD1, and the learning program PG1. The derived model DM1 generated through the process PS5 may be generated by processing a model. The learning process PS5 may be a process using various learning methods, such as transfer learning.

4. Other Embodiments

The processes according to the embodiments and modifications as described above may be embodied in various different forms (modifications) other than the embodiments and modifications as described above. For example, the surgery support system 1 need not always include all of the components of the surgery room system 5100. The surgery support system 1 may include only components that are needed to analyze a risk as described above and output an analysis result. In this case, the surgery support system 1 may include only the information processing apparatus 100 that performs the analysis process and the surgery room system that provides the surgery image to the information processing apparatus 100 and outputs the analysis result. Then, the surgery room system may include only a camera (endoscope or the like) as an imaging means for capturing the surgery image, an apparatus (CCU or the like) that performs image processing (signal processing) of superimposing information on an image, and an output apparatus (monitor or the like) that outputs the information. The above-described configuration is one example, and the surgery support system 1 may adopt any apparatus configuration as long as it is possible to analyze a risk as described above and output the analysis result. For example, if the information processing apparatus 100 performs image processing (signal processing) of superimposing information on an image in the surgery support system 1, the surgery room system need not include an apparatus that performs the image processing (signal processing).

4-1. Other Configuration Examples

In the above-described example, the case has been described in which the apparatus that functions as the output unit for outputting information is included in the surgery room system 5100; however, the output unit need not always be included in the surgery room system 5100. This will be described below. Explanation of the same components and the same functions as those of the surgery support system 1 and the information processing apparatus 100 according to the embodiment will be omitted appropriately.

<4-1-1. Modification of Surgery Support System>

Figure 13:
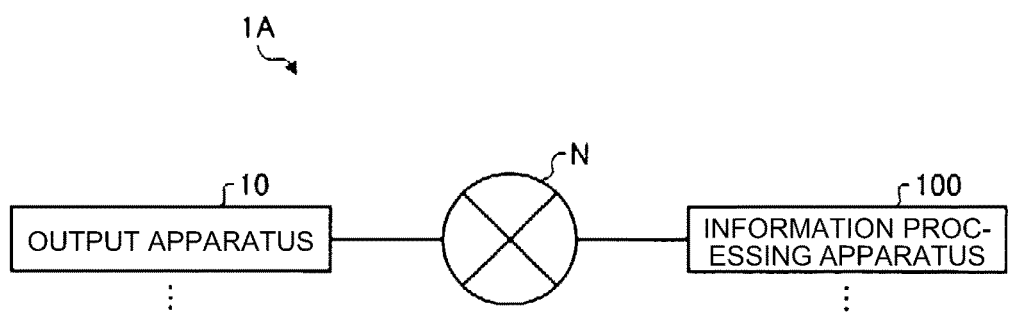
FIG. 13 is a diagram illustrating a configuration example of an information processing system according to a modification of the present disclosure.

For example, the output unit may be provided separately from the surgery room system 5100 and the information processing apparatus 100. This will be described below with reference to FIG. 13. FIG. 13 is a diagram illustrating a configuration example of an information processing system according to a modification of the present disclosure.

As illustrated in FIG. 13, a surgery support system 1A includes an output apparatus 10 and the information processing apparatus 100. The output apparatus 10 and the information processing apparatus 100 are communicably connected to each other via a predetermined communication network (network N) in a wired or wireless manner. FIG. 13 is a diagram illustrating a configuration example of the surgery support system according to the embodiment. The surgery support system 1A illustrated in FIG. 13 may include the plurality of output apparatuses 10 or the plurality of information processing apparatuses 100. The surgery support system 1A may include the surgery room system 5100. In this case, the information processing apparatus 100 or the output apparatus 10 performs a process of superimposing the surgery support information on the surgery image that is the first surgery, by appropriately using various techniques related to image formation, image processing, or the like.

The output apparatus 10 outputs the surgery support information that is based on the risk analysis information, in a superimposed manner on the surgery image. The output apparatus 10 displays various kinds of information. The output apparatus 10 includes, for example, a liquid crystal display, an organic EL display, or the like. The output apparatus 10 displays the surgery support information that is based on the risk analysis information, in a superimposed manner on the surgery image. The output apparatus 10 displays the surgery support information that is based on the risk analysis information generated by the information processing apparatus 100, in a superimposed manner on the surgery image. For example, the output apparatus 10 displays the surgery support information that is based on the risk analysis information generated by the information processing apparatus 100, in a superimposed manner on the surgery image acquired from the surgery room system 5100.

For example, the output apparatus 10 displays the image IM11, the mark MK11, or the like. The output apparatus 10 displays the mark MK11 that is the surgery support information, in a superimposed manner on the image IM11 that is the surgery image. If the output apparatus 10 outputs the surgery support information by voice, the output apparatus 10 has a function to output voice. For example, the output apparatus 10 includes a speaker that outputs voice.

The output apparatus 10 includes a communication unit that is realized by, for example, a NIC, a communication circuit, or the like, is connected to the network N (the Internet or the like) in a wired or wireless manner, and transmits and receives information to and from the information processing apparatus 100, the surgery room system 5100, or the like via the network N.

For example, the output apparatus 10 is a computer (information processing apparatus) that executes a process of outputting the surgery support information. A processor of the output apparatus 10 may be various processors, such as a CPU, a GPU, or an FPGA. For example, the output apparatus 10 includes a control unit that is realized by a CPU, a GPU, an FPGA, or the like, and executes various kinds of information processing, such as an output process.

The output apparatus 10 functions as the output unit. The output apparatus 10 outputs the surgery support information that is based on the risk analysis information generated by the analysis unit 133, in a superimposed manner on the first surgery image. The output apparatus 10 outputs the surgery support information that is based on the risk analysis information, in a superimposed manner on the surgery image of the first surgery.

The output apparatus 10 outputs the surgery support information that is the information indicating a position of a risk site, in a superimposed manner on the surgery image of the first surgery. The output apparatus 10 outputs the surgery support information that is superimposed on a position that does not overlap with the risk site, in a superimposed manner on the surgery image of the first surgery. The output apparatus 10 outputs, in a superimposed manner, the surgery support information at a position that does not overlap with the risk site in the surgery image of the first surgery.

The output apparatus 10 outputs the surgery support information that is information indicating at least one of a probability and severity of a risk, in a superimposed manner on the surgery image of the first surgery. The output apparatus 10 outputs the surgery support information with a predetermined shape or color, in a superimposed manner on the surgery image of the first surgery.

The output apparatus 10 outputs the surgery support information for which the shape or the color is changed in accordance with at least one of a probability and severity of a risk, in a superimposed manner on the surgery image of the first surgery. The output apparatus 10 outputs the surgery support information for which at least one of movement and blinking is performed on the surgery image, in a superimposed manner on the surgery image of the first surgery.

The output apparatus 10 outputs the surgery support information for which at least one of a moving speed and motion is controlled in accordance with at least one of a probability and severity of a risk, in a superimposed manner on the surgery image of the first surgery. The output apparatus 10 outputs the surgery support information for which content is dynamically changed on the basis of at least one of surgery duration and a surgery scene, in a superimposed manner on the surgery image of the first surgery.

The output apparatus 10 outputs the surgery support information for which display is controlled based on a predetermined criterion, in a superimposed manner on the surgery image of the first surgery. The output apparatus 10 outputs the surgery support information that is displayed after a lapse of a predetermined period since notice is given by voice, in a superimposed manner on the surgery image of the first surgery.

The output apparatus 10 outputs the surgery support information that is displayed for a predetermined period during surgery, in a superimposed manner on the surgery image of the first surgery. The output apparatus 10 outputs the surgery support information for a predetermined period during surgery, in a superimposed manner on the surgery image of the first surgery.

In the case of a special light observation image, the output apparatus 10 outputs the surgery support information that is displayed in a predetermined mode, in a superimposed manner on the surgery image of the first surgery. In the case of a special light observation image, the output apparatus 10 outputs the surgery support information in a predetermined mode, in a superimposed manner on the surgery image of the first surgery.

<4-1-2. Modification of Information Processing Apparatus>

Figure 14:
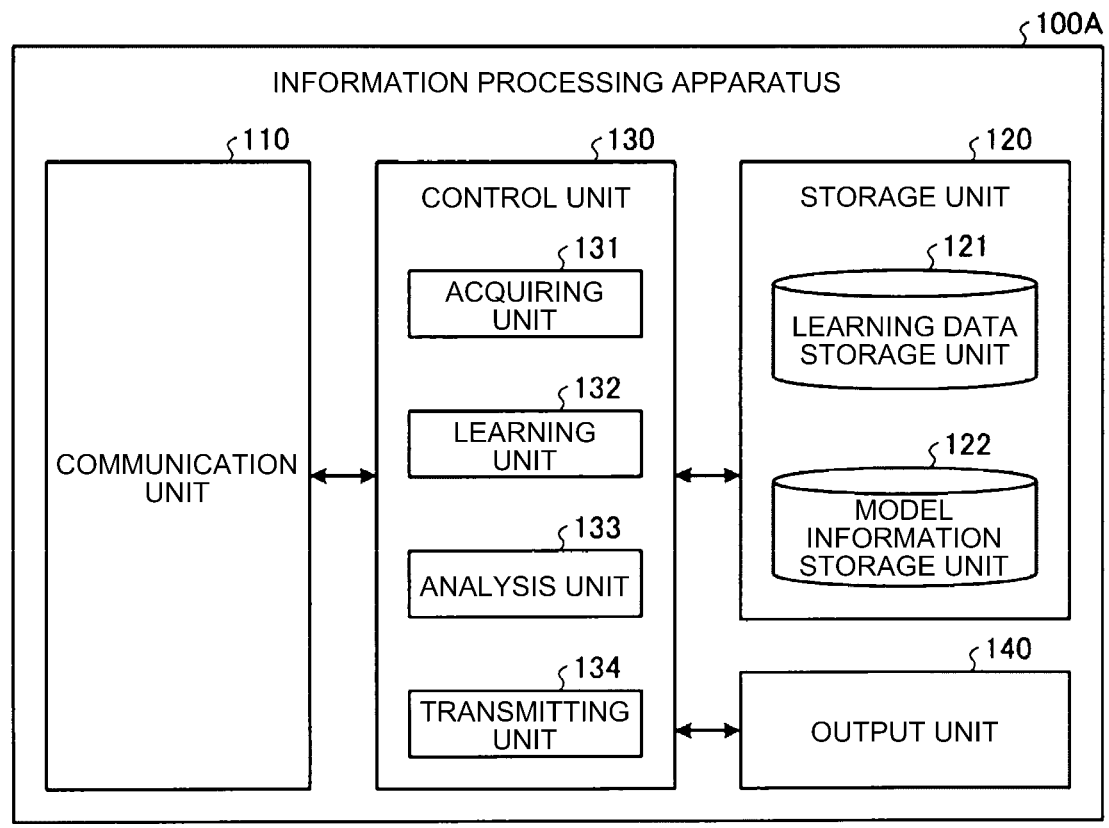
FIG. 14 is a diagram illustrating a configuration example of the information processing apparatus according to the modification of the present disclosure.

The information processing apparatus may be configured to include the output unit. This will be described below with reference to FIG. 14. FIG. 14 is a diagram illustrating a configuration example of an information processing apparatus according to a modification of the present disclosure. In this case, an information processing apparatus 100A performs a process of superimposing the surgery support information on the surgery image of the first surgery, by appropriately using various techniques related to image formation, image processing, or the like.

As illustrated in FIG. 14, the information processing apparatus 100A includes the communication unit 110, the storage unit 120, the control unit 130, and an output unit 140. The information processing apparatus 100A causes the communication unit 110 to transmit and receive information to and from the surgery room system 5100 or the like via the network N. For example, the analysis unit 133 performs a process of superimposing the surgery support information on the surgery image of the first surgery, by appropriately using various techniques related to image formation, image processing, or the like.

The output unit 140 outputs various kinds of information. The output unit 140 outputs various kinds of information generated by the analysis unit 133. The output unit 140 outputs the surgery support information that is based on the risk analysis information. The output unit 140 outputs various kinds of information acquired from the surgery room system 5100.

The output unit 140 displays various kinds of information. The output unit 140 is realized by, for example, a liquid crystal display, an organic EL display, or the like. The output unit 140 may be realized by any means as long as it is possible to display the surgery support information based on the risk analysis information in a superimposed manner on the surgery image.

For example, the output unit 140 displays the image IM11, the mark MK11, or the like. The output unit 140 displays the mark MK11 that is the surgery support information, in a superimposed manner on the image IM11 that is the surgery image. If the surgery support information is to be output by voice, the output unit 13 has a function to output voice. For example, the output unit 13 includes a speaker that outputs voice.

The output unit 140 outputs the surgery support information that is based on the risk analysis information generated by the analysis unit 133, in a superimposed manner on the surgery image. The output unit 140 outputs the surgery support information that is based on the risk analysis information, in a superimposed manner on the surgery image of the first surgery.

The output unit 140 outputs the surgery support information that is information indicating a position of a risk site, in a superimposed manner the surgery image of the first surgery. The output unit 140 outputs the surgery support information that is superimposed on a position that does not overlap with the risk site, in a superimposed manner on the surgery image of the first surgery. The output unit 140 outputs, in a superimposed manner, the surgery support information at a position that does not overlap with the risk site in the surgery image of the first surgery.

The output unit 140 outputs the surgery support information that is information indicating at least one of a probability and severity of a risk, in a superimposed manner the surgery image of the first surgery. The output unit 140 outputs the surgery support information with a predetermined shape or color, in a superimposed manner on the surgery image of the first surgery.

The output unit 140 outputs the surgery support information for which the shape or the color is changed in accordance with at least one of a probability and severity of a risk, in a superimposed manner on the surgery image of the first surgery. The output unit 140 outputs the surgery support information for which at least one of movement and blinking is performed on the surgery image, in a superimposed manner on the surgery image of the first surgery.

The output unit 140 outputs the surgery support information for which at least one of a moving speed and motion is controlled in accordance with at least one of a probability and severity of a risk, in a superimposed manner on the surgery image of the first surgery. The output unit 140 outputs the surgery support information for which content is dynamically changed on the basis of at least one of surgery duration and a surgery scene, in a superimposed manner on the surgery image of the first surgery.

The output unit 140 outputs the surgery support information for which display is controlled based on a predetermined criterion, in a superimposed manner on the surgery image of the first surgery. The output unit 140 outputs the surgery support information that is displayed after a lapse of a predetermined period since notice is given by voice, in a superimposed manner on the surgery image of the first surgery.

The output unit 140 outputs the surgery support information that is displayed for a predetermined period during surgery, in a superimposed manner on the surgery image of the first surgery. The output unit 140 outputs the surgery support information for a predetermined period during surgery, in a superimposed manner on the surgery image of the first surgery.

In the case of a special light observation image, the output unit 140 outputs the surgery support information that is displayed in a predetermined mode, in a superimposed manner on the surgery image of the first surgery. In the case of a special light observation image, the output unit 140 outputs the surgery support information in a predetermined mode, in a superimposed manner on the surgery image of the first surgery.

4-2. Output Mode of Surgery Support Information

The output of the surgery support information as described above need not always be performed by displaying information, but may be performed in various output modes. For example, the output of the surgery support information as described above may be output by voice (voice output). In this case, in a state in which the surgery image is displayed on an apparatus, such as a display, that displays information, the surgery support information is output as voice, so that the surgery support information is output in a superimposed manner on the surgery image.

As described above, the output of the surgery support information in a superimposed manner on the surgery image (may also be referred to as "superimposed output") is a concept that includes not only display of the information on a screen, such as a display, in a superimposed manner, but also output in a temporally superimposed manner. In other words, the superimposed output described herein is a concept that includes operation of providing pieces of information in different output modes in a temporally superimposed manner, such as display of the surgery image and voice output of the surgery support information.

4-3. Others

Of the processes described in the embodiments, all or part of a process described as being performed automatically may also be performed manually. Alternatively, all or part of a process described as being performed manually may also be performed automatically by known methods. In addition, the processing procedures, specific names, and information including various types of data and parameters illustrated in the above-described document and drawings may be arbitrarily changed unless otherwise specified. For example, various kinds of information illustrated in the drawings are not limited to the information as illustrated in the drawings.

In addition, the constituent elements illustrated in the drawings are functionally conceptual and do not necessarily have to be physically configured in the manner illustrated in the drawings. In other words, specific forms of distribution and integration of the apparatuses are not limited to those illustrated in the drawings, and all or part of the apparatuses may be functionally or physically distributed or integrated in arbitrary units depending on various loads or use conditions.

Further, each of the embodiments and the modifications as described above may be appropriately combined as long as the processes do not conflict with each other.

Furthermore, the effects described in this specification are merely illustrative or exemplified effects, and are not limitative, and other effects may be achieved.

5. Effects According to Present Disclosure

As described above, the surgery support system according to the present disclosure (the surgery support system 1 in the embodiment) includes an acquiring unit (the acquiring unit 131 in the embodiment), an analysis unit (the analysis unit 133 in the embodiment), and an output unit (the display apparatus 5155, the output apparatus 10, the output unit 140, or the like in the embodiment). The acquiring unit acquires the first surgery image that is a surgery image. In some examples, the analysis unit generates the risk analysis information on the first surgery image by applying the first surgery image acquired by the acquiring unit to a trained model that is generated using learning data including the second surgery image that is a surgery image different from the first surgery image and including information on a complication risk due to surgery. The output unit outputs the surgery support information that is based on the risk analysis information generated by the analysis unit, in a superimposed manner on the surgery image.

Therefore, the surgery support system according to the present disclosure generates the risk analysis information on the first surgery image by applying the first surgery image to the trained model, and outputs the surgery support information based on the generated risk analysis information in a superimposed manner on the surgery image, to thereby be able to output the surgery support information in a superimposed manner on a surgery image of ongoing surgery, for example. In this manner, the surgery support system is able to appropriately output the information for supporting surgery by outputting the surgery support information in a superimposed manner on the surgery image.

Further, in some examples, the analysis unit generates risk analysis information indicating a complication risk due to the first surgery corresponding to the first surgery image. The output unit outputs the surgery support information that is based on the risk analysis information, in a superimposed manner on the surgery image of the first surgery. Therefore, the surgery support system is able to appropriately output the information for supporting surgery by outputting the surgery support information on a complication risk due to the first surgery corresponding to the first surgery image, in a superimposed manner on the surgery image of the first surgery.

Furthermore, the acquiring unit acquires the trained model that is generated using learning data including information on a complication risk due to the second surgery corresponding to the second surgery image. In some examples, the analysis unit generates the risk analysis information by inputting the first surgery image to the trained model acquired by the acquiring unit. Accordingly, the surgery support system is able to generate the risk analysis information on the first surgery image with accuracy by using the trained model that is trained based on a combination of the second surgery image and the complication risk due to the second surgery corresponding to the second surgery image. Therefore, the surgery support system is appropriately output the information for supporting surgery by outputting, in a superimposed manner on the surgery image, the surgery support information that is based on the accurate risk analysis information.

Moreover, the second surgery image is image information including a site that becomes a cause of a surgical complication. Accordingly, the surgery support system is able to generate the risk analysis information on the first surgery image related to the site that becomes a cause of a surgical complication, by using the trained model that is trained based on the image including the site that becomes a cause of a surgical complication. Therefore, the surgery support system is able to appropriately output the information for supporting surgery by outputting, in a superimposed manner on the surgery image, the surgery support information that is based on the risk analysis information on the site that becomes a cause of a surgical complication.

Furthermore, the second surgery image is image information including at least one of a suture site and a bleeding site. Accordingly, the surgery support system is able to generate the risk analysis information on the first surgery image related to at least one of the suture site and the bleeding site, by using the trained model that is trained based on the image including at least one of the suture site and the bleeding site. Therefore, the surgery support system is able to appropriately output the information for supporting surgery by outputting, in a superimposed manner on the surgery image, the surgery support information that is based on the risk analysis information on at least one of the suture site and the bleeding site.

Moreover, the information on a complication risk is information on a risk occurrence site. Accordingly, the surgery support system is able to generate the risk analysis information on the first surgery image related to the risk occurrence site, by using the trained model that is trained based on the information on the risk occurrence site. Therefore, the surgery support system is able to appropriately output the information for supporting surgery by outputting, in a superimposed manner on the surgery image, the surgery support information that is based on the risk analysis information on the risk occurrence site.

Furthermore, the information on a risk occurrence site is information on at least one of a suture site and a bleeding site. Accordingly, the surgery support system is able to generate the risk analysis information on the first surgery image related to at least one of the suture site and the bleeding site, by using the trained model that is trained based on at least one of the suture site and the bleeding site. Therefore, the surgery support system is able to appropriately output the information for supporting surgery by outputting, in a superimposed manner on the surgery image, the risk analysis information that is based on at least one of the suture site and the bleeding site.

Moreover, the surgery support system includes a learning unit (the learning unit 132 in the embodiment). In some examples, the learning unit uses, as teaching data, the second surgery image that is a past surgery image and information on a complication risk due to surgery, and generates, through machine learning, a trained model as a determination model that adopts a surgery image as an input and adopts a complication risk due to surgery as an output. Accordingly, the surgery support system is able to generate a trained model that outputs information used to determine a complication risk in surgery corresponding to a surgery image when the surgery image is input. Then, the surgery support system outputs the surgery support information that is based on the risk analysis information, which is generated by applying the first surgery image to the trained model, in a superimposed manner on the surgery image. Therefore, the surgery support system is able to appropriately output the information for supporting surgery by outputting the surgery support information in a superimposed manner on the surgery image.

Furthermore, the learning data includes feature information on a surgery video. Accordingly, the surgery support system is able to generate the risk analysis information on the first surgery image in which a feature of the surgery video is reflected, by using the trained model that is trained based on the feature information on the surgery video including a surgery image or the like. Therefore, the surgery support system is able to appropriately output the information for supporting surgery by outputting, in a superimposed manner on the surgery image, the surgery support information that is based on the risk analysis information in which the feature of the surgery video is reflected.

Moreover, the feature information is at least one of a change of manipulation and a change of a surgery scene. Accordingly, the surgery support system is able to generate the risk analysis information on the first surgery image in which at least one of the change of the manipulation and the change of the surgery scene is reflected, by using the trained model that is trained based on the feature information including at least one of the change of the manipulation and the change of the surgery scene. Therefore, the surgery support system is able to appropriately output the information for supporting surgery by outputting, in a superimposed manner on the surgery image, the surgery support information that is based on the risk analysis information in which at least one of the change of the manipulation and the change of the surgery scene is reflected.

Furthermore, the feature information is a suture process including at least one of a suture method and a suture position. Accordingly, the surgery support system is able to generate the risk analysis information on the first surgery image in which the suture process including at least one of the suture method and the suture position is reflected, by using the trained model that is trained based on the feature information including the suture process that includes at least one of the suture method and the suture position. Therefore, the surgery support system is able to appropriately output the information for supporting surgery by outputting, in a superimposed manner on the surgery image, the surgery support information that is based on the risk analysis information in which the suture process is reflected.

Moreover, the risk analysis information includes information on the risk occurrence site. Accordingly, by generating the risk analysis information including the information on the risk occurrence site and outputting the surgery support information based on the generated risk analysis information in a superimposed manner on the surgery image, the surgery support system is able to output the surgery support information including the information on the risk occurrence site in a superimposed manner on, for example, a surgery image of ongoing surgery. In this manner, the surgery support system is able to appropriately output the information for supporting surgery by outputting, in a superimposed manner on the surgery image, the surgery support information including the information on the risk occurrence site.

Furthermore, the risk analysis information is information including information on at least one of a ruptured suture site and a bleeding site and including at least one of a probability and severity of a complication risk at the site. Accordingly, by generating the risk analysis information including the ruptured suture, the bleeding site, one of the probability and the severity of the complication risk at the site, and the like, and outputting the surgery support information based on the generated risk analysis information in a superimposed manner on the surgery image, the surgery support system is able to output the surgery support information including the ruptured suture, the bleeding site, one of the probability and the severity of the complication risk at the site, and the like, in a superimposed manner on, for example, the surgery image of ongoing surgery. In this manner, the surgery support system is able to appropriately output the information for supporting surgery by outputting, in a superimposed manner on the surgery image, the surgery support information including the ruptured suture, the bleeding site, one of the probability and the severity of the complication risk at the site, and the like.

Moreover, the surgery support information is information indicating a position of a risk site. Accordingly, by outputting the surgery support information indicating the position of the risk site in a superimposed manner on the surgery image, the surgery support system is able to output the surgery support information indicating the position of the risk site, in a superimposed manner on, for example, the surgery image of ongoing surgery. In this manner, by outputting the surgery support information indicating the position of the risk site in a superimposed manner on the surgery image, the surgery support system allows a medical professional, such as a surgeon (doctor), who performs surgery to appropriately recognize the risk site. Therefore, the surgery support system is able to appropriately output the information for supporting surgery.

Furthermore, the surgery support information is superimposed on a position that does not overlap with the risk site. Accordingly, by outputting the surgery support information in a superimposed manner on a position that does not overlap with the risk site in the surgery image, the surgery support system allows a surgeon or the like who performs surgery to appropriately recognize the risk site without disturbing treatment on the risk site. Therefore, the surgery support system is able to appropriately output the information for supporting surgery.

Moreover, a shape or a color of the surgery support information is changed in accordance with at least one of a probability and severity of a risk. Accordingly, by outputting the surgery support information with a predetermined shape or color, it is possible to allow a surgeon or the like who performs surgery to appropriately recognize the surgery support information. For example, by outputting the surgery support information for which the shape or the color is changed in accordance with at least one of the probability and the severity of a risk, the surgery support system is able to allow a surgeon or the like who performs surgery to appropriately recognize the surgery support information. Therefore, the surgery support system is able to appropriately output the information for supporting surgery.

Furthermore, the surgery support system includes the information processing apparatus (the information processing apparatus 100 in the embodiment) that includes the acquiring unit and the analysis unit, and the output apparatus (the display apparatus 5155, the output apparatus 10, or the like in the embodiment) that functions as the output unit. Accordingly, the surgery support system is able to appropriately output the information for supporting surgery, by causing the output apparatus to output the surgery support information generated by the information processing apparatus, in a superimposed manner on the surgery image.

6. Hardware Configuration

Figure 15:
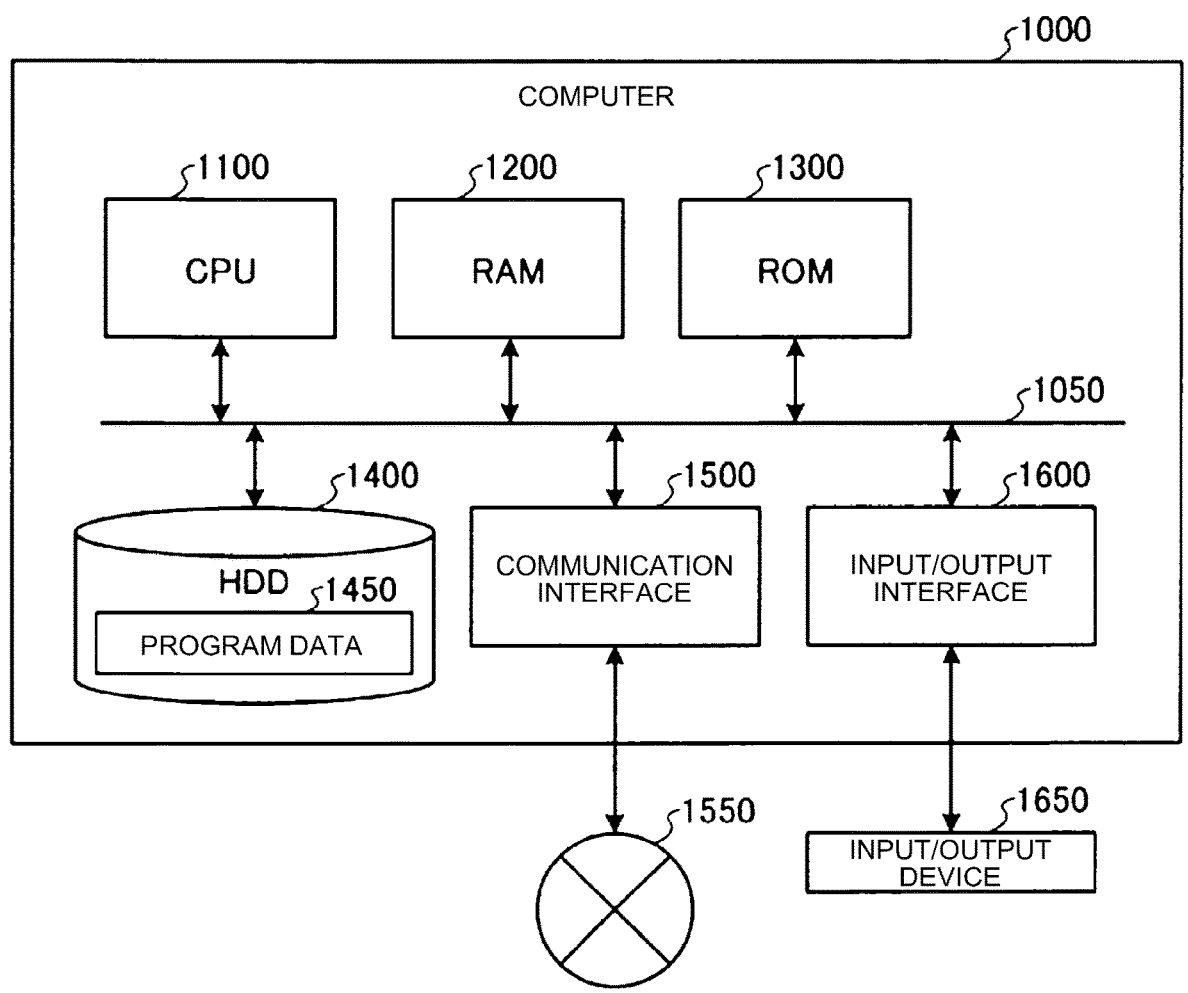
FIG. 15 is a hardware configuration diagram illustrating an example of a computer that implements functions of the information processing apparatus.

An information apparatus, such as the information processing apparatus 100 according to the embodiments and the modifications as described above, is realized by a computer 1000 configured as illustrated in FIG. 15, for example. FIG. 15 is a diagram illustrating a hardware configuration example of the computer 1000 that implements the functions of the information processing apparatus, such as the information processing apparatus 100. The information processing apparatus 100 according to the embodiment will be described below as one example. The computer 1000 includes a CPU 1100, a RAM 1200, a read only memory (ROM) 1300, a hard disk drive (HDD) 1400, a communication interface 1500, and an input/output interface 1600. All of the units of the computer 1000 are connected to one another via a bus 1050.

The CPU 1100 operates based on programs stored in the ROM 1300 or the HDD 1400 and controls each of the units. For example, the CPU 1100 loads the programs stored in the ROM 1300 or the HDD 1400 onto the RAM 1200 and performs processes corresponding to the various programs.

The ROM 1300 stores therein a boot program, such as basic input output system (BIOS), that is executed by the CPU 1100 when the computer 1000 is activated, a program that depends on hardware of the computer 1000, or the like.

The HDD 1400 is a computer-readable recording medium that permanently stores therein programs executed by the CPU 1100, data used by the programs, and the like. Specifically, the HDD 1400 is a recording medium that stores therein the information processing program according to the present disclosure as one example of program data 1450.

The communication interface 1500 is an interface that enables the computer 1000 to connect to an external network 1550 (for example, the Internet). For example, the CPU 1100 receives data from other apparatuses and transmits data generated by the CPU 1100 to other apparatuses, via the communication interface 1500.

The input/output interface 1600 is an interface for connecting an input/output device 1650 and the computer 1000. For example, the CPU 1100 receives data from an input device, such as a keyboard or a mouse, via the input/output interface 1600. Further, the CPU 1100 transmits data to an output device, such as a display, a speaker, or a printer, via the input/output interface 1600. Furthermore, the input/output interface 1600 may function as a media interface that reads a program or the like stored in a predetermined recording medium (media). Examples of the media include an optical recording medium, such as a digital versatile disk (DVD) and a phase change rewritable disk (PD), a magneto-optical (MO) recording medium, such as an MO disk, a tape medium, a magnetic recording medium, and a semiconductor memory. For example, when the computer 1000 functions as the information processing apparatus 100 according to the embodiment, the CPU 1100 of the computer 1000 executes the information processing program loaded on the RAM 1200, to thereby implement the functions of the control unit 130 or the like. Further, the HDD 1400 stores therein the information processing program according to the present disclosure and data stored in the storage unit 120. The CPU 1100 reads and executes the program data 1450 from the HDD 1400; however, as another example, it may be possible to acquire the programs from a different apparatus via the external network 1550.

Additionally, the present technology may also be configured as below.

(1)
A surgery support system including:
an acquiring unit configured to acquire a first surgery image that is a surgery image;
an analysis unit configured to generate risk analysis information on the first surgery image by applying the first surgery image acquired by the acquiring unit to a trained model that is generated using learning data, the learning data including a second surgery image that is a surgery image different from the first surgery image and including information on a complication risk due to surgery; and
an output unit configured to output surgery support information that is based on the risk analysis information generated by the analysis unit, in a superimposed manner on a surgery image.

(2)
The surgery support system according to (1), in which
the analysis unit generates the risk analysis information indicating the complication risk due to first surgery corresponding to the first surgery image, and
the output unit outputs the surgery support information that is based on the risk analysis information, in a superimposed manner on the surgery image of the first surgery.

(3)
The surgery support system according to (1) or (2), in which
the acquiring unit acquires the trained model that is generated using the learning data including the information on the complication risk due to second surgery corresponding to the second surgery image, and
the analysis unit generates the risk analysis information by inputting the first surgery image to the trained model acquired by the acquiring unit.

(4)
The surgery support system according to any one of (1) to (3), in which the first surgery image is high-quality low-latency image information that meets an image quality condition on image quality and a latency condition on latency.

(5)
The surgery support system according to any one of (1) to (4), in which the first surgery image is image information with resolution of 4K or higher.

(6)
The surgery support system according to any one of (1) to (5), in which the first surgery image is a special light observation image.

(7)
The surgery support system according to any one of (1) to (6), in which the second surgery image is image information including a site that becomes a cause of a surgical complication.

(8)
The surgery support system according to (7), in which the second surgery image is image information including at least one of a suture site and a bleeding site.

(9)
The surgery support system according to (7) or (8), in which the second surgery image is image information including the site that is detected by image recognition.

(10)
The surgery support system according to any one of (1) to (9), in which the second surgery image is a special light observation image.

(11)
The surgery support system according to (10), in which the second surgery image is an image in which an internal state of one of a suture site and a bleeding site is visualized.

(12)
The surgery support system according to any one of (1) to (11), in which the information on the complication risk is information indicating at least one of a probability and severity of a complication.

(13)
The surgery support system according to (12), in which the probability is binary information indicating whether the complication is present or absent.

(14)
The surgery support system according to (12) or (13), in which the severity is five-grade information indicating a degree of impact of the complication.

(15)
The surgery support system according to any one of (1) to (14), in which the information on the complication risk is information on a risk occurrence site.

(16)
The surgery support system according to (15), in which the information on the risk occurrence site is information on at least one of a suture site and a bleeding site.

(17)
The surgery support system according to any one of (1) to (16), further including a learning unit configured to use, as teaching data, the second surgery image that is a past surgery image and information on a complication risk due to surgery, and generate, through machine learning, the trained model as a determination model that adopts a surgery image as an input and adopts a complication risk due to surgery as an output.

(18)
The surgery support system according to (17), in which the learning unit generates the trained model by using deep learning as the machine learning.

(19)
The surgery support system according to any one of (1) to (18), in which the learning data includes feature information on a surgery video.

(20)
The surgery support system according to (19), in which the feature information indicates at least one of a change of manipulation and a change of a surgery scene.

(21)
The surgery support system according to (19) or (20), in which the feature information indicates a suture process including at least one of a suture method and a suture position.

(22)
The surgery support system according to (21), in which the suture process is detected based on a trajectory of a surgical tool.

(23)
The surgery support system according to (22), in which the suture process is detected based on a temporal change of a position of a distal end of the surgical tool.

(24)
The surgery support system according to any one of (19) to (23), in which the feature information is detected based on operating time of surgery.

(25)
The surgery support system according to any one of (1) to (24), in which the analysis unit generates the risk analysis information by adopting the first surgery image subjected to a correction process to the trained model.

(26)
The surgery support system according to (25), in which the correction process is a process related to at least one of rotation, distortion, and resolution.

(27)
The surgery support system according to any one of (1) to (26), in which the risk analysis information is information including at least one of a probability and severity of a complication risk.

(28)
The surgery support system according to any one of (1) to (27), in which the risk analysis information includes information on a risk occurrence site.

(29)
The surgery support system according to (28), in which the risk analysis information is information including information on at least one of a ruptured suture site and a bleeding site and including at least one of a probability and severity of a complication risk at a site.

(30)
The surgery support system according to any one of (1) to (29), in which a predetermined process in risk analysis is performed by a cloud server.

(31)
The surgery support system according to any one of (1) to (30), in which the risk analysis information is information in which information having a trade-off relationship with ruptured suture is taken into account.

(32)
The surgery support system according to any one of (1) to (31), in which the surgery support information is information indicating a position of a risk site.

(33)
The surgery support system according to (32), in which the surgery support information is superimposed on a position that does not overlap with a risk site.

(34)
The surgery support system according to any one of (1) to (33), in which the surgery support information is information indicating at least one of a probability and severity of a risk.

(35)
The surgery support system according to any one of (1) to (34), in which the surgery support information has a predetermined shape or a predetermined color.

(36)
The surgery support system according to (35), in which one of the shape and the color of the surgery support information is changed in accordance with at least one of a probability and severity of a risk.

(37)
The surgery support system according to any one of (1) to (36), in which the surgery support information is subjected to at least one of movement and blinking on the surgery image.

(38)
The surgery support system according to (37), in which at least one of a moving speed and motion of the surgery support information is controlled in accordance with at least one of a risk probability and severity.

(39)
The surgery support system according to any one of (1) to (38), in which a content of the surgery support information is dynamically changed on the basis of at least one of surgery duration and a surgery scene.

(40)
The surgery support system according to any one of (1) to (39), in which display of the surgery support information is controlled on the basis of a predetermined criterion.

(41)
The surgery support system according to any one of (1) to (40), in which the surgery support information is displayed after a lapse of a predetermined period since notice is given by voice.

(42)
The surgery support system according to any one of (1) to (41), in which the surgery support information is displayed for a predetermined period during surgery.

(43)
The surgery support system according to any one of (1) to (42), in which the surgery support information is displayed in a predetermined mode in a case of a special light observation image.

(44)
The surgery support system according to any one of (1) to (43), in which input data and learning data of the trained model are surgery videos.

(45)
The surgery support system according to any one of (1) to (44), in which input data and learning data of the trained model are time-series images.

(46)
The surgery support system according to any one of (1) to (45), in which a surgery difficulty level varies depending on one of a disease, a site, and a surgery procedure.

(47)
The surgery support system according to any one of (1) to (46), in which an external state of suture is observed using normal light and an internal state of suture is observed using special light.

(48)
The surgery support system according to any one of (1) to (47), further including:
an information processing apparatus including the acquiring unit and the analysis unit; and
an output apparatus configured to function as the output unit.

(49)
A surgery support method including:
acquiring a first surgery image that is a surgery image;
generating risk analysis information on the first surgery image by applying the acquired first surgery image to a trained model that is generated using learning data, the learning data including a second surgery image that is a surgery image different from the first surgery image and including information on a complication risk due to surgery; and
outputting surgery support information that is based on the generated risk analysis information, in a superimposed manner on a surgery image.

(50)
The information processing apparatus including
an acquiring unit configured to acquire a first surgery image that is a surgery image; and
an analysis unit configured to generate risk analysis information on the first surgery image by applying the first surgery image acquired by the acquiring unit to a trained model that is generated using learning data, the learning data including a second surgery image that is a surgery image different from the first surgery image and including information on a complication risk due to surgery.

(51)
An information processing program causing a computer to execute:
acquiring a first surgery image that is a surgery image; and
generating risk analysis information on the first surgery image by applying the acquired first surgery image to a trained model that is generated using learning data, the learning data including a second surgery image that is a surgery image different from the first surgery image and including information on a complication risk due to surgery.

(52)
A ruptured suture determination system including:
a classifier that is a multi-layer neural network having a predetermined parameter and classifies whether input data indicates ruptured suture; and
an output unit that outputs whether ruptured suture is present on the basis of classification performed by the classifier, in which
the predetermined parameter is a parameter that is generated by performing machine learning by a multi-layer neural network using learning data, the learning data being generated based on a suture image in which a suture portion appears and being added with a label indicating whether the learning data is a ruptured suture.

Further example arrangements are defined by the following numbered clauses:

1. A surgery support system including:
an acquiring unit configured to acquire a first surgery image;
an analysis unit configured to generate risk analysis information from the first surgery image by applying the first surgery image acquired by the acquiring unit to a trained model generated using learning data, the learning data including a second surgery image different from the first surgery image, the second surgery image having associated information on a complication risk due to surgery; and
an output unit configured to output surgery support information that is based on the risk analysis information generated by the analysis unit, in a superimposed manner on the first surgery image.

2. The surgery support system according to clause 1, wherein
the analysis unit generates the risk analysis information indicating the complication risk due to first surgery corresponding to the first surgery image, and
the output unit outputs the surgery support information that is based on the risk analysis information, in a superimposed manner on the first surgery image of the first surgery.

3. The surgery support system according to clause 1 or clause 2, wherein
the acquiring unit acquires the trained model generated using the learning data including the information on the complication risk due to second surgery corresponding to the second surgery image, and
the analysis unit generates the risk analysis information by inputting the first surgery image to the trained model acquired by the acquiring unit.

4. The surgery support system according to any one of the preceding clauses, wherein the second surgery image is image information including a site that became a cause of a surgical complication.

5. The surgery support system according to clause 4, wherein the second surgery image includes image information including at least one of a suture site and a bleeding site.

6. The surgery support system according to any one of the preceding clauses, wherein the information on the complication risk includes information on a risk occurrence site.

7. The surgery support system according to clause 6, wherein the information on the risk occurrence site includes information on at least one of a suture site and a bleeding site.

8. The surgery support system according to any one of the preceding clauses, further including:
a learning unit configured to use, as teaching data, the second surgery image that is a past surgery image and associated information on a complication risk due to surgery, and to generate, through machine learning, the trained model as a determination model that adopts a surgery image as an input and generates a complication risk due to surgery as an output.

9. The surgery support system according to any one of the preceding clauses, wherein the learning data includes feature information on a surgery video.

10. The surgery support system according to clause 9, wherein the feature information includes at least one of a change of manipulation and a change of a surgery scene.

11. The surgery support system according to clause 9 or clause 10, wherein the feature information indicates a suture process including at least one of a suture method and a suture position.

12. The surgery support system according to any one of the preceding clauses, wherein the risk analysis information includes information on a risk occurrence site.

13. The surgery support system according to clause 12, wherein the risk analysis information is information including information on at least one of a ruptured suture site and a bleeding site and including at least one of a probability and severity of a complication risk at a site.

14. The surgery support system according to any one of the preceding clauses, wherein the surgery support information includes information indicating a position of a risk site.

15. The surgery support system according to clause 14, wherein the output unit is configured to superimpose the surgery support information on a position that does not overlap with the risk site.

16. The surgery support system according to any one of the preceding clauses, wherein the output unit is configured to change one of a shape and a color of the surgery support information in accordance with at least one of a probability and severity of a risk.

17. The surgery support system according to any one of the preceding clauses, further including:
an information processing apparatus including the acquiring unit and the analysis unit; and
an output apparatus configured to function as the output unit.

18. A surgery support method including:
acquiring a first surgery image;
generating risk analysis information from the first surgery image by applying the acquired first surgery image to a trained model that is generated using learning data, the learning data including a second surgery image that is different from the first surgery image, the second surgery image having associated information on a complication risk due to surgery; and
outputting surgery support information that is based on the generated risk analysis information, in a superimposed manner on the first surgery image.

19. An information processing apparatus including:
an acquiring unit configured to acquire a first surgery image; and
an analysis unit configured to generate risk analysis information from the first surgery image by applying the first surgery image acquired by the acquiring unit to a trained model that is generated using learning data, the learning data including a second surgery image that is different from the first surgery image, the second surgery image having associated information on a complication risk due to surgery.

20. An information processing program causing a computer to execute:
acquiring a first surgery image; and
generating risk analysis information from the first surgery image by applying the acquired first surgery image to a trained model that is generated using learning data, the learning data including a second surgery image that is different from the first surgery image, the second surgery image having associated information on a complication risk due to surgery.

REFERENCE SIGNS LIST

1 Surgery support system
5100 Surgery room system
5155 Display apparatus
100 Information processing apparatus
110 Communication unit
120 Storage unit
121 Learning data storage unit
122 Model information storage unit
130 Control unit
131 Acquiring unit
132 Learning unit
133 Analysis unit
134 Transmitting unit

The invention claimed is:

1. A surgery support system comprising:
circuitry configured to:
acquire a first surgery image;
generate risk analysis information from the first surgery image by applying the first surgery image acquired to a trained model generated using learning data, the learning data including a second surgery image different from the first surgery image, the second surgery image having associated information on a complication risk due to surgery and includes a risk site that became a cause of a surgical complication; and
output surgery support information that is based on the risk analysis information generated, in a superimposed manner on the first surgery image, wherein the surgery support information includes information indicating a position of the risk site.

2. The surgery support system according to claim 1, wherein
the risk analysis information indicates the complication risk due to first surgery corresponding to the first surgery image, and
the surgery support information is based on the risk analysis information is to be superimposed on the first surgery image of the first surgery.

3. The surgery support system according to claim 1, wherein
the trained model is generated using the learning data including the information on the complication risk due to second surgery corresponding to the second surgery image, and
the circuitry is to generate the risk analysis information by inputting the first surgery image to the trained model acquired.

4. The surgery support system according to claim 1, wherein the second surgery image comprises image information including at least one of a suture site and a bleeding site.

5. The surgery support system according to claim 1, wherein the information on the complication risk comprises information on the risk occurrence site.

6. The surgery support system according to claim 5, wherein the information on the risk occurrence site comprises information on at least one of a suture site and a bleeding site.

7. The surgery support system according to claim 1, further comprising:
a learning circuit configured to use, as teaching data, the second surgery image that is a past surgery image and associated information on a complication risk due to surgery, and to generate, through machine learning, the trained model as a determination model that adopts a surgery image as an input and generates a complication risk due to surgery as an output.

8. The surgery support system according to claim 1, wherein the learning data includes feature information on a surgery video.

9. The surgery support system according to claim 8, wherein the feature information comprises at least one of a change of manipulation and a change of a surgery scene.

10. The surgery support system according to claim 8, wherein the feature information indicates a suture process including at least one of a suture method and a suture position.

11. The surgery support system according to claim 1, wherein the risk analysis information is information including information on at least one of a ruptured suture site and a bleeding site identified as the risk site and including at least one of a probability and severity of a complication risk at the risk site.

12. The surgery support system according to claim 1, wherein the circuitry is configured to superimpose the surgery support information on a position that does not overlap with the risk site.

13. The surgery support system according to claim 1, wherein the circuitry is configured to change one of a shape and a color of the surgery support information in accordance with at least one of a probability and severity of a risk.

14. The surgery support system according to claim 1, further comprising:
an information processing apparatus including the circuitry; and
a display configured to display the output surgery support information superimposed on the first surgery image.

15. A surgery support method comprising:
acquiring a first surgery image;
generating risk analysis information from the first surgery image by applying the acquired first surgery image to a trained model that is generated using learning data, the learning data including a second surgery image that is different from the first surgery image, the second surgery image having associated information on a complication risk due to surgery and includes a risk site that became a cause of a surgical complication; and
outputting surgery support information that is based on the generated risk analysis information, in a superimposed manner on the first surgery image, wherein the surgery support information includes information indicating a position of a risk site.

16. An information processing apparatus comprising:
an acquiring circuitry configured to acquire a first surgery image;
an analysis circuitry configured to generate risk analysis information from the first surgery image by applying the first surgery image acquired by the acquiring circuitry to a trained model that is generated using learning data, the learning data including a second surgery image that is different from the first surgery image, the second surgery image having associated information on a complication risk due to surgery and includes a risk site that became a cause of a surgical complication; and
an output circuit configured to output surgery support information including information indicating a position of a risk site.

17. The information processing apparatus according to claim 16, wherein the output circuit is configured to superimpose the surgery support information on a position that does not overlap with the risk site.

18. The information processing apparatus according to claim 16, wherein the output circuit is configured to change one of a shape and a color of the surgery support information in accordance with at least one of a probability and severity of a risk.

19. The information processing apparatus according to claim 16, wherein the risk site includes at least one of a suture site and a bleeding site.

20. A non-transitory recording medium storing an information processing program causing a computer to execute:
acquiring a first surgery image; and
generating risk analysis information from the first surgery image by applying the acquired first surgery image to a trained model that is generated using learning data, the learning data including a second surgery image that is different from the first surgery image, the second surgery image having associated information on a complication risk due to surgery and includes a risk site that became a cause of a surgical complication; and
outputting surgery support information including information indicating a position of a risk site.

* * * * *